US012740719B2

(12) United States Patent
Similä et al.

(10) Patent No.: US 12,740,719 B2
(45) Date of Patent: Sep. 22, 2026

(54) TECHNIQUES FOR HEART RATE DETECTION

(71) Applicant: Oura Health Oy, Oulu (FI)

(72) Inventors: Heidi Similä, Oulu (FI); Xi Zhang, Daly City, CA (US); Tero Juhani Vallius, Kontio (FI); Jussi Petteri Järvelä, Kempele (FI); Juha-Pekka Syrjälä, Oulu (FI); Tommi Heinonen, Oulu (FI); Pauli Ensio Tikkanen, Liminka (FI)

(73) Assignee: Oura Health Oy, Oulu (FI)

( * ) Notice: Subject to any disclaimer, the term of this patent is extended or adjusted under 35 U.S.C. 154(b) by 634 days.

(21) Appl. No.: 17/957,345

(22) Filed: Sep. 30, 2022

(65) Prior Publication Data

US 2023/0107454 A1 Apr. 6, 2023

Related U.S. Application Data

(60) Provisional application No. 63/251,086, filed on Oct. 1, 2021.

(51) Int. Cl.
*A61B 5/00* (2006.01)
*A61B 5/024* (2006.01)

(52) U.S. Cl.
CPC ...... *A61B 5/02438* (2013.01); *A61B 5/02433* (2013.01); *A61B 5/7221* (2013.01)

(58) Field of Classification Search
CPC ............ A61B 5/02438; A61B 5/02433; A61B 5/7221
See application file for complete search history.

(56) References Cited

U.S. PATENT DOCUMENTS 10,568,525 B1 2/2020 Wu et al.
10,973,423 B2 4/2021 Jain et al.
(Continued)

FOREIGN PATENT DOCUMENTS

EP 3491999 A2 6/2019
JP 2001-041531 A 2/2001
(Continued)

OTHER PUBLICATIONS

International Search Report and Written Opinion—PCT/US2022/045428—ISA/EPO—Feb. 8, 2023.
(Continued)

*Primary Examiner* — Joel F Brutus
(74) *Attorney, Agent, or Firm* — ArentFox Schiff LLP

(57) ABSTRACT

Methods, systems, and devices for heart rate detection are described. A method may include receiving physiological data associated with the user, where the physiological data may include motion data and temperature data collected throughout a time interval via a wearable device associated with the user. The method may include determining a condition quality metric associated with the time interval based on the received motion data and temperature data. The condition quality metric may indicate a relative quality of the physiological data collected throughout the time interval for determination of heart rate measurements. The method may include sampling photoplethysmogram (PPG) data for the user via the wearable device based on the condition quality metric satisfying a threshold metric value and a timer satisfying a first threshold time duration. The method may include determining a heart rate measurement for the user based at least in part on the sampled PPG data.

20 Claims, 15 Drawing Sheets

(56) References Cited

U.S. PATENT DOCUMENTS

| | | | | |
|---|---|---|---|---|
| 11,051,706 | B1 | 7/2021 | Nadeau et al. | |
| 11,096,601 | B2 | 8/2021 | Hong et al. | |
| 2011/0152637 | A1 | 6/2011 | Kateraas et al. | |
| 2014/0031652 | A1 | 1/2014 | Baker, Jr. | |
| 2014/0275854 | A1 | 9/2014 | Venkatraman | |
| 2014/0358012 | A1* | 12/2014 | Richards | H04W 4/027 600/479 |
| 2015/0201853 | A1 | 7/2015 | Hong et al. | |
| 2016/0354017 | A1 | 12/2016 | Meehan et al. | |
| 2017/0209055 | A1 | 7/2017 | Pantelopoulos | |
| 2017/0296075 | A1* | 10/2017 | Loseu | A61B 5/02416 |
| 2017/0311825 | A1* | 11/2017 | Weekly | A61B 5/6815 |
| 2018/0000424 | A1* | 1/2018 | Demirtas | G16H 50/30 |
| 2018/0317788 | A1 | 11/2018 | Jain et al. | |
| 2018/0325457 | A1 | 11/2018 | Ghosh et al. | |
| 2019/0053754 | A1 | 2/2019 | Gowda et al. | |
| 2019/0110755 | A1 | 4/2019 | Vincenzo et al. | |
| 2020/0359971 | A1 | 11/2020 | Wenyi et al. | |

FOREIGN PATENT DOCUMENTS

| | | | |
|---|---|---|---|
| JP | 2006-312010 | A | 11/2006 |
| JP | 2009-047324 | A | 3/2009 |
| JP | 2010-099383 | A | 5/2010 |
| JP | 2011-520517 | A | 7/2011 |
| JP | 2017-131445 | A | 8/2017 |
| WO | 2017/001955 | A1 | 1/2017 |
| WO | 2017/190051 | A1 | 11/2017 |
| WO | 2021/064212 | A1 | 4/2021 |

OTHER PUBLICATIONS

Schramm, W. M., et al., “Effect of local limb temperature on pulse oximetry and the plethysmographic pulse wave.”, International journal of clinical monitoring and computing, vol. 14, Apr. 4, 2016, pp. 17-22.

Japan Patent Office, “Office Action,” issued in connection with Japan Patent Application No. 2024-519674 dated Sep. 2, 2025 (11 pages) (6 pages of English Translation and 5 pages of Original Document).

Japan Patent Office, “JP Decision to Grant,” issued in connection with Japan Patent Application No. 2024-519674 dated Jan. 20, 2026 (3 pages).

Office Action received for Indian Patent Application No. 202417026349, mailed on Mar. 12, 2026, 11 pages.

Third Party Submission received for Indian Patent Application No. 202417026349, mailed on May 20, 2025, 349 pages.

European Search Report and Opinion received for EP Application No. 25209537.7, mailed on Mar. 27, 2026, 5 pages.

* cited by examiner

PPG Channel Selection

500

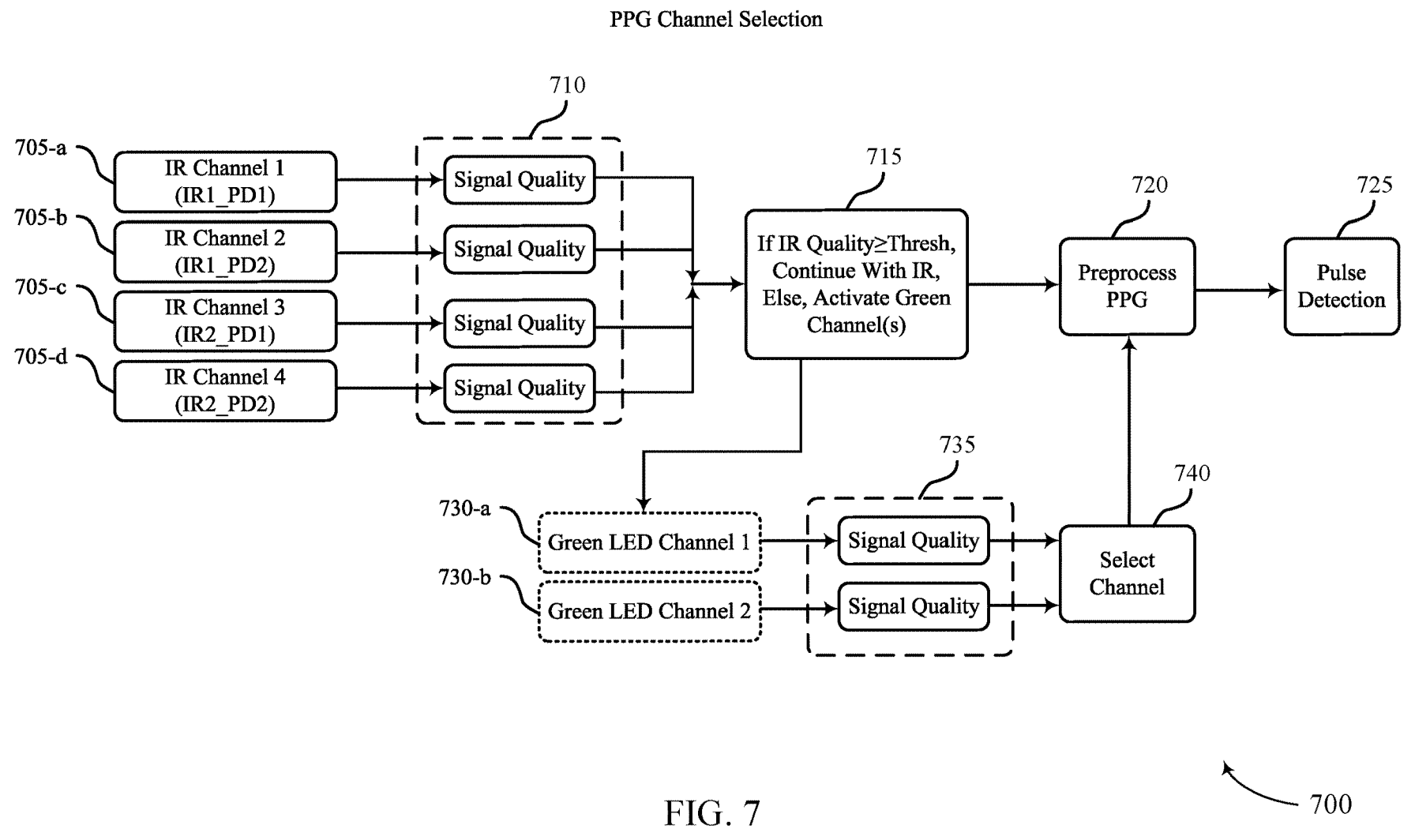

PPG Channel Selection

700

705-a IR Channel 1 (IR1_PD1)
705-b IR Channel 2 (IR1_PD2)
705-c IR Channel 3 (IR2_PD1)
705-d IR Channel 4 (IR2_PD2)

710 Signal Quality
Signal Quality
Signal Quality
Signal Quality

715 If IR Quality≥Thresh, Continue With IR, Else, Activate Green Channel(s)

720 Preprocess PPG

725 Pulse Detection 730-a Green LED Channel 1
730-b Green LED Channel 2

735 Signal Quality
Signal Quality

740 Select Channel

FIG. 7

TECHNIQUES FOR HEART RATE DETECTION

CROSS REFERENCE

The present Application for Patent claims the benefit of U.S. Provisional Patent Application No. 63/315,602 by SIMILA et al., entitled "TECHNIQUES FOR HEART RATE DETECTION," filed Mar. 2, 2022, assigned to the assignee hereof, and U.S. Provisional Patent Application No. 63/251,086 by SIMILA et al., entitled "TECHNIQUES FOR HEART RATE DETECTION," filed Oct. 1, 2021, assigned to the assignee hereof, and expressly incorporated by reference herein.

FIELD OF TECHNOLOGY

The following relates to wearable devices and data processing, including techniques for heart rate detection.

BACKGROUND

Some wearable devices may be configured to collect data from users associated with heart rate of the user, such as motion data, temperature data, photoplethysmogram (PPG) data, etc. In some cases, some wearable devices may be configured to detect one or more sets of data under preconfigured conditions. Conventional techniques for detecting data in accordance with preconfigured conditions may be improved.

BRIEF DESCRIPTION OF THE DRAWINGS

FIGS. 5 through 7 illustrate examples of channel selection procedures that support techniques for heart rate detection in accordance with aspects of the present disclosure.

DETAILED DESCRIPTION

Figure 1:
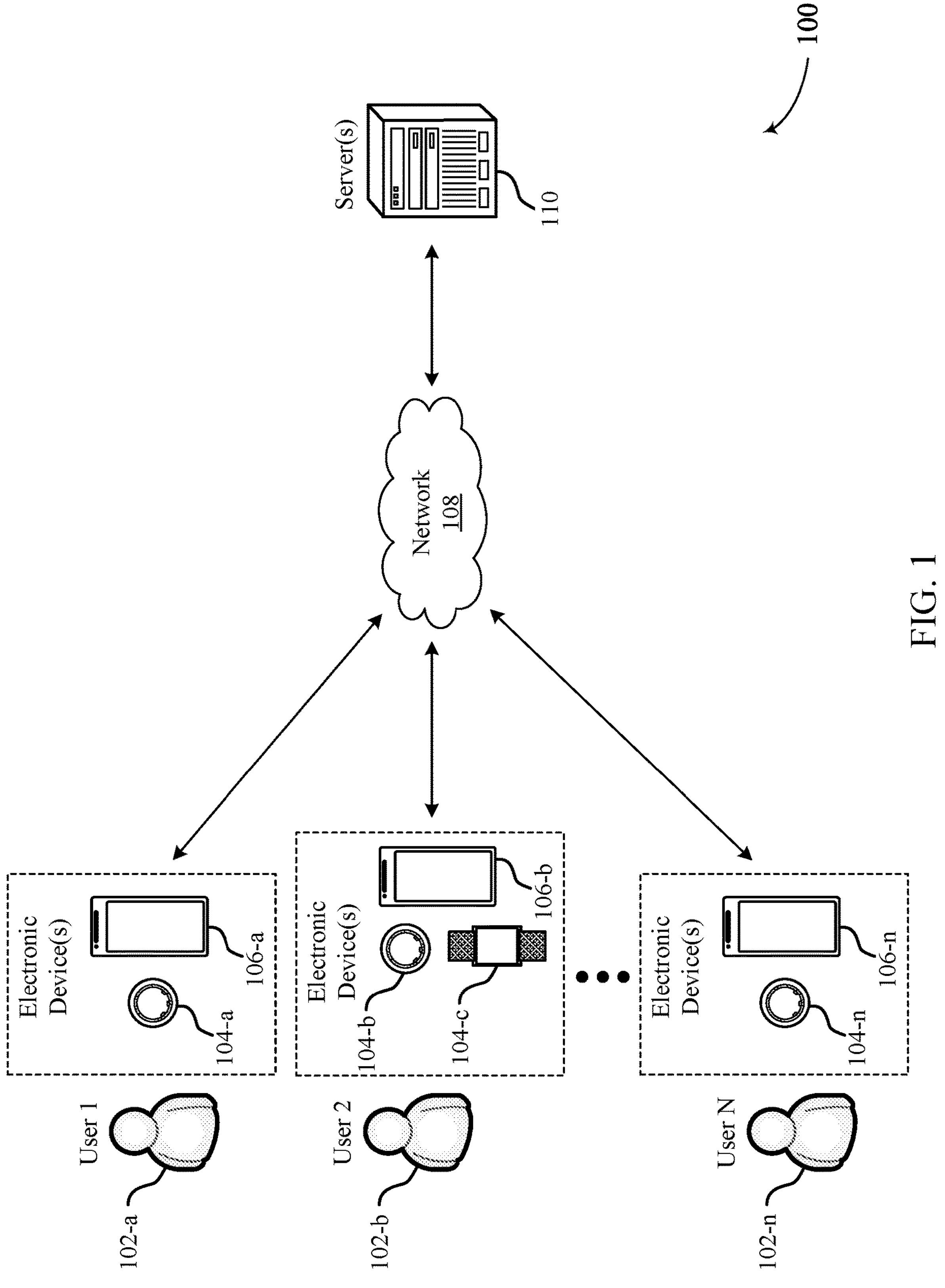
FIG. 1 illustrates an example of a system that supports techniques for heart rate detection in accordance with aspects of the present disclosure.

A user may use a device (e.g., a wearable device) to determine physiological measurements of the user, such as heart rate. A resting heart rate (RHR) may refer to a number of times a user's heart beats per minute during periods of "rest," such as periods that a user is refraining from activity, such as while sleeping, meditating, or otherwise relaxing. RHR may be used to determine a sleep quality, recovery, stress response, activity level, and overall health of a user. To measure a heart rate of a user, such as a RHR, a wearable device may use photoplethysmography (PPG) to measure a heart rate for a user over time. For example, a wearable device may measure RHR of a user by detecting changes in blood pulse volume through PPG sensors in the wearable device (e.g., infrared (IR) PPG sensors, infrared light emitting diodes (LEDs)). Each time that a user's heart beats, blood is pumped out to the arteries located in the user's hands and fingers. The PPG sensors are able to detect these changes in blood flow (e.g., arterial flow, venous blood flow) and volume using light reflection and absorption. Each pulse causes the arteries in a user's finger to alternate between swelling and contracting. By shining a light on the skin of the user, particularly on the skin of a finger, changes in light absorbed by the blood and reflected back from the wavering volume of red blood cells in the arteries are accounted for. From here, PPG can represent these blood flow changes through a visual waveform that represents the activity of the user's heart (e.g., heart rate).

In some cases, a wearable device may determine heart rate variability (HRV) of a user. HRV is a measure of variation in time (e.g., milliseconds) between heart beats, and may be used as an indication of how a user's body is balancing the two branches of the autonomic nervous systems: the sympathetic and parasympathetic, and may thus represent a user's current ability to manage stress, provide an indication of illness or exhaustion in the user, etc. A wearable device may calculate HRV using the root mean square of successive differences (rMSSD) between heart beats. The rMSSD may be obtained by first calculating each successive time difference between heartbeats in ms. Then, each of the values is squared and the result is averaged before the square root of the total is obtained. The rMSSD reflects the beat-to-beat variance in HR and thus is used as a measure of HRV.

Heart rate (e.g., RHR) and HRV are sensitive metrics that are subject to change based on activities being performed by a user (e.g., drinking a glass of water, standing up, watching television). Certain activities may result in a spike or dip in heart rate, HRV, or both, and such variations may be referred to as noise in the data. During periods of rest, that a user is refraining from performing activities, particularly during periods of sleep, the body is in a stable state (e.g., the most stable state within a 24-hour period) thereby resulting in reduced variation associated with heart rate and HRV. Accordingly, some wearable devices may measure heart (e.g., RHR), HRV, or both of a user during periods of rest (e.g., during periods of reduced noise) to determine accurate heart rate and HRV data. However, determining heart rate measurements only during periods of rest may greatly reduce the quantity of heart rate measurements that may be collected for a user throughout any given time period. As such, some conventional wearable devices may not efficiently track a user's heart rate throughout the day, and may provide only a limited depiction of the user's heart rate, and therefore a limited depiction of the user's overall health.

Techniques described herein are directed to wearable devices configured with an ability to measure heart rate data irrespective of whether a user is resting (e.g., during periods the user is awake, during periods of activity, or rest). Accordingly, the wearable device may determine heart rate data for a user during active periods, restful periods, or a combination thereof, so as to provide a more complete representation of a user's heart rate, HRV, or both over time. The wearable devices described herein may be configured with a procedure for measuring heart data (e.g., while a user is active, while a user is not resting, while a user is not sleeping, during the day) while reducing noise in the data.

A procedure for determining heart rate (e.g., non-sleep data, daytime data, or a combination of daytime and night-time data) may include a wearable device measuring physiological data associated with the user, such as temperature and motion data. In some cases, to mitigate power consumption of a wearable device, the wearable device may use the physiological data to detect moments for measuring PPG. For example, rather than measuring PPG constantly, a wearable device may use physiological data of the user to detect moments that may result in PPG data that meets a quality threshold. Upon detecting moments for measuring PPG data, the wearable device may measure PPG for a duration and assess that PPG signal quality. If the PPG signal quality meets a threshold quality, then the wearable device may estimate the heart rate of the user based on the PPG data. Accordingly, the procedures described herein may be configured to determine accurate heart rate data while conserving power of the wearable device.

For example, a method may include receiving physiological data associated with the user, where the physiological data may include motion data and temperature data collected throughout a time interval via a wearable device associated with the user. The method may include determining a condition quality metric associated with the time interval based on the received motion data and temperature data. The condition quality metric may indicate a relative quality of the physiological data collected throughout the time interval for determination of heart rate measurements. The method may include sampling PPG data for the user via the wearable device based on the condition quality metric satisfying a threshold metric value and a timer satisfying a first threshold time duration. The method may include determining a heart rate measurement for the user based on the sampled PPG data.

In some implementations, the procedure for determining heart rate may include selecting one or more "channels" for sampling the PPG data (e.g., a PPG sensor). For example, the wearable device may be configured with multiple PPG sensors, where a PPG sensor may include an emitter (e.g., LED), a receiver (e.g., photodetector), or both, where a pair of PPG sensors including at least one emitter and at least one receive makes up an optical path (e.g., channel) used for PPG measurement. In some cases, a PPG sensor may refer to one or more green LEDs, one or more red LEDs, one or more IR LEDs, or any other set of LEDs. In some aspects, some PPG sensors may exhibit better signal quality in some circumstances as compared to other sensors. For example, green LEDs may result in the highest quality heart rate measurements in many circumstances, where IR diodes may provide better quality in other circumstances, such as in cases of high movement or cold skin temperatures. In this regard, some aspects of the present disclosure are directed to techniques that enable the wearable device to "test" which PPG sensors/channels exhibit the best signal quality, and therefore select PPG sensors/channels that will be used for heart rate measurements.

In this regard, the wearable device may be configured to select one or more PPG sensors for obtaining the PPG data based on a signal quality associated with the one or more selected sensors, and/or the signal quality associated with the other PPG sensors (non-selected PPG sensors). In some cases, the wearable device may be configured to analyze a set of one or more PPG sensors (e.g., a subset or all of the PPG sensors configured to the wearable device). For example, the wearable device may determine (e.g., measure, calculate) a quality of the output from each PPG sensor. In some cases, the wearable device may be configured to compare the signal quality of each PPG sensor to one or more signal quality thresholds and/or compare the signal quality of each PPG sensor to the other determined signal qualities. For example, the wearable device may select the PPG sensor associated with the highest signal quality and/or select one or more PPG sensors that satisfy the one or more signal quality thresholds. For instance in some cases, the wearable device may measure signals from each green LED and each IR channel, compare the signal qualities, and select whether heart rate measurements will be performed using green LEDs or IR diodes.

In some cases, the wearable device may be configured with a default PPG sensor (e.g., a particular PPG sensor) or a default PPG sensor type (e.g., one or more IR LEDs, green LEDS, etc.) to use for sampling PPG data. The wearable device may determine whether the default PPG sensor(s) satisfies a signal quality threshold. If the default PPG sensor(s) satisfy the threshold, then the wearable device may use the default PPG sensor(s) to sample the PPG data. If, however, the default PPG sensor(s) fail to satisfy the threshold, then the wearable device may switch to and/or analyze a second set of one or more PPG sensors. For example, if the default PPG sensors do not satisfy the threshold, then the wearable device may be configured to use the second set of one or more PPG sensors to sample PPG data. In another example, if the default PPG sensors do not satisfy the threshold, then the wearable device may be configured to determine whether the second set of one or more PPG sensors satisfy a signal quality threshold. Accordingly, the wearable device may select one or more PPG sensors to sample the PPG data to improve the PPG data based on signal quality.

In some cases, the signal quality criteria to be used for selecting a PPG sensor may be based on a use case. The signal quality criteria may be based on one or more parameters, where the one or more parameters may include an illness of the user (e.g., pneumonia), a disease of the user (e.g., apnea, Atrial fibrillation (AFib)), a current workout, a previous workout, or a planned future workout, etc. For example, one or more of the parameters may be associated with a different type of signal, signal shape, etc., and thus, the signal quality criteria may change based on the one or more parameters. Therefore, the device may identify the one or more parameters (e.g., use cases) that apply, if any, and determine the signal quality criteria to use for selecting one or more PPG sensors.

In some implementations, the procedure for determining heart rate may include a method for outputting heart rate data based on comparing the heart rate data to heart rate criteria (e.g., one or more thresholds) so as to improve heart rate data provided to the user. If the heart rate data satisfies the heart rate criteria, then the device may output the heart rate data to the user. In the case that the heart rate data fails to satisfy the heart rate criteria, the device may refrain from outputting the heart rate data. In such cases, a "gap" in the heart rate data may occur, even though the data may be accurate and reliable.

In order to mitigate the occurrence of gaps in the output heart rate data, the wearable device may be configured with multiple sets of criteria (e.g., multiple threshold), where a latter criteria is relaxed from a former criteria of the multiple sets. For example, a first set of criteria may be associated with the strictest criteria, the second set of criteria may be less strict than the first set but stricter than a third set, and so on. Accordingly, the device may first compare measurement data to the first set of criteria and if the data satisfies the first set of criteria, the device may output the heart rate data. If the data fails to satisfy the first set, the device may then compare the heart rate data to the second set of criteria, and so on. In some cases, the device may label the outputted data with a quality label. For example, heart rate data that passed the second set of criteria but not the first set of criteria may not be as reliable as data that passed the first set of criteria, and so the device may label all data, the most reliable data, or any data that failed to pass the first criteria with a label indicative of the quality of the output data. As such, the device may provide heart rate data to the user without gaps, or with minimal gaps in the data.

Aspects of the disclosure are initially described in the context of systems supporting physiological data collection from users via wearable devices. Aspects are then described with reference to heart rate determination procedures, channel selection procedure, and a graphical user interface (GUI). Aspects of the disclosure are further illustrated by and described with reference to apparatus diagrams, system diagrams, and flowcharts that relate to techniques for heart rate detection.

FIG. 1 illustrates an example of a system 100 that supports techniques for heart rate detection in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow, venous blood flow, etc. within the user's finger. In particular, a ring 104 may utilize one or more LEDs (e.g., red LEDs, green LEDs) which emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models which are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for determining heart rate data of a user based on physiological data (e.g., motion data, temperature data) collected by a wearable device. The system may support techniques for determining heart rate data, irrespective of whether the user is in a resting state, etc. In particular, the system 100 illustrated in FIG. 1 may support techniques for determining heart rate data of a user 102, and causing a user device 106 corresponding to the user 102 to display an indication of the heart rate data. In some cases, displaying the heart rate data may be based on comparing, prior to display, heart rate data to a set of one or more thresholds so as to display the heart rate data based on a quality of the data. In some cases, determining the quality of the data may be performed in accordance with an iterative (e.g., tiered) comparison procedure.

For example, as shown in FIG. 1, User 1 (user 102-*a*) may be associated with a wearable device 104-*a* (e.g., ring 104-*a*) and a user device 106-*a*. In this example, the ring 104-*a* may collect data associated with the user 102-*a*, including motion, temperature, heart rate, HRV, and the like. In some aspects, the ring 104-*a* may be used to collect physiological data of the user that the ring 104-*a* may use to determine whether to perform PPG monitoring. In some cases, wearable device 105-*a* may select a channel (e.g., a set of one or more sensors) for collecting the PPG data. For example, wearable device 104-*a* may be configured with multiple PPG sensors, where a PPG sensor may be an emitter (e.g., LED) and receiver (e.g., photodetector) pair which make up an optical path (e.g., channel) for PPG measurement. In some cases, a PPG sensor may refer to one or more green LEDs, one or more red LEDs, one or more IR LEDs, or any other set of LEDs and may select one or more PPG sensors for obtaining the PPG data based on a signal quality associated with one or more of the PPG sensors.

The ring 104-*a* may determine heart rate data based on the PPG monitoring. Physiological data collection, PPG monitoring, and heart rate data determination may be performed by any of the components of the system 100, including the ring 104-*a*, the user device 106-*a* associated with User 1, the one or more servers 110, or any combination thereof. Upon determination of heart rate data, the system 100 may selectively cause the GUI of the user device 106-*a* to display all or a subset of the heart rate data.

It should be appreciated by a person skilled in the art that one or more aspects of the disclosure may be implemented in a system 100 to additionally or alternatively solve problems other than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
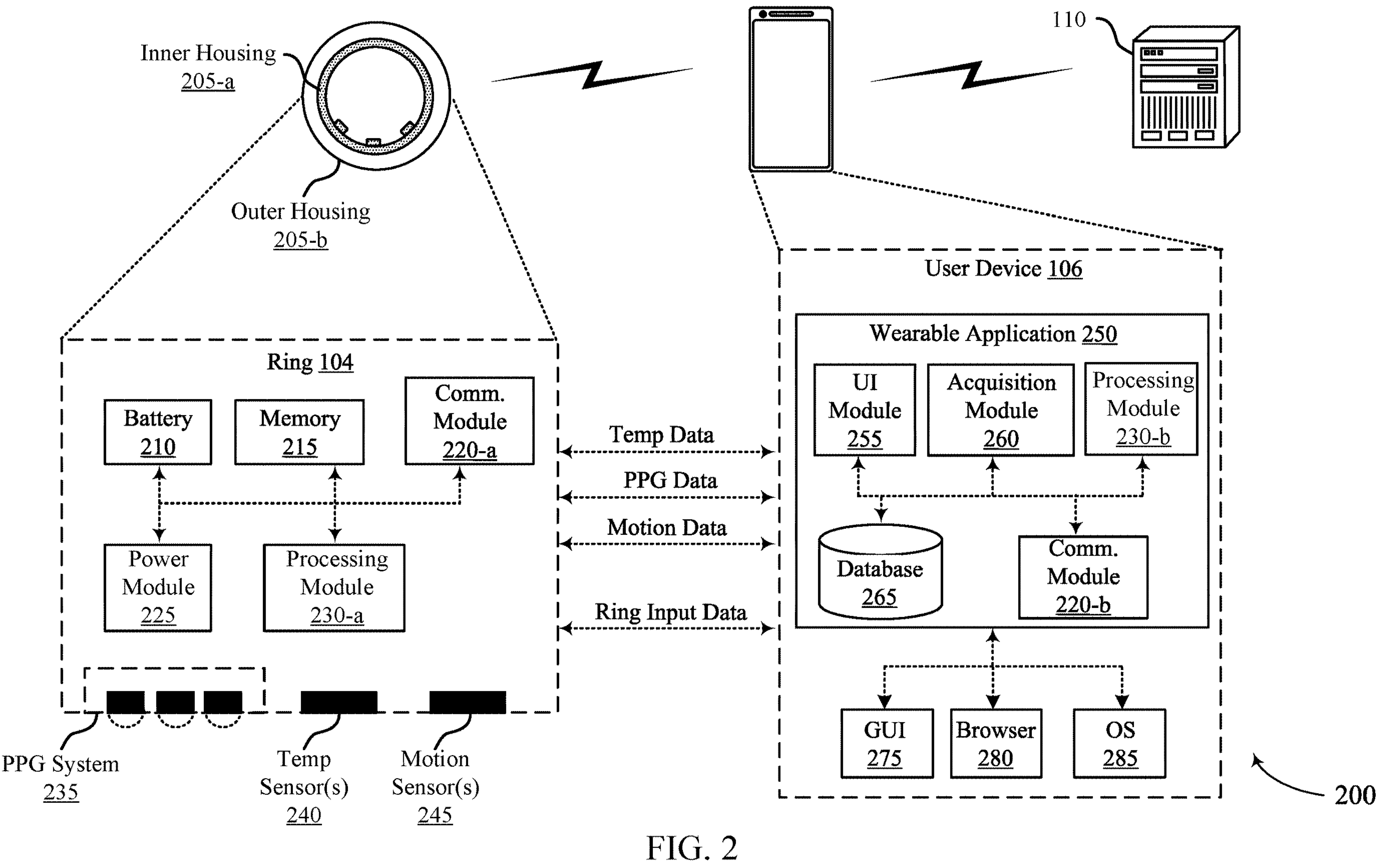
FIG. 2 illustrates an example of a system that supports techniques for heart rate detection in accordance with aspects of the present disclosure.

FIG. 2 illustrates an example of a system 200 that supports techniques for heart rate detection in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components which are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, which may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors which may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBls. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner which is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for determining heart rate data of a user based on physiological data (e.g., motion data, temperature data) collected by a wearable device. In some aspects, the ring 104, user device 106, and servers 110 of the system 200 may be configured to determine heart rate data of a user, irrespective of whether the user in a resting state, etc. In particular, the respective components of the system 200 may be used to determine heart rate data of a user based on physiological data of the user (e.g., motion, temperature). For example, the respective components of the system 200 may determine moments when to measure PPG, and thus heart rate to ensure that the PPG and heart rate data meets a quality threshold based on the physiological data. As such, the moments may be detected by leveraging sensors on the ring 104 of the system 200.

For example, as noted previously herein, the ring 104 of the system 200 may be worn by a user to collect data from the user, including temperature, heart rate, movement, and the like. The ring 104 of the system 200 may collect the physiological data from the user based on arterial blood flow, venous blood flow, etc. Physiological data collected by the ring 104 may be used to determine when to collect PPG and heart rate data by the system 200. The system 200 may selectively cause the GUI 275 of the user device 106 to display all or a subset of the heart rate data.

In some cases, the system 200 may select a channel (e.g., a set of one or more sensors) for collecting the PPG data. For example, the ring 104 may be configured with multiple PPG sensors, where a PPG sensor may be an emitter (e.g., LED) and receiver (e.g., photodetector) pair which constructs an optical path (e.g., channel). In some cases, a PPG sensor may refer to one or more green LEDs, one or more red LEDs, one or more IR LEDs, or any other set of LEDs and may select one or more PPG sensors for obtaining the PPG data based on a signal quality associated with one or more of the PPG sensors.

For example, in some implementations, the ring 104 may simultaneously measure signal qualities for each green LED channel and each IR channel, compare the signal qualities, and select the channel (e.g., select a green LED channel, select an IR channel) with the best signal quality that will be used for heart rate measurements. By way of another example, in other cases, the ring 104 may measure a signal quality of IR channels, and may utilize IR channels for heart rate measurement if the signal quality of the IR channel(s) is above a quality threshold, or utilize other channels (e.g., green LED channels) if the signal quality of the IR channel(s) is below the quality threshold.

In some cases, displaying the heart rate data may be based on comparing, prior to display, heart rate data to a set of one or more thresholds so as to display the heart rate data based on a quality of the data. In some cases, determining the quality of the data may be performed in accordance with an iterative (e.g., tiered) comparison procedure. The procedure for determining heart rate data may be further shown and described with reference to FIGS. 3 through 8.

Figure 3:
FIGS. 3 and 4 illustrate examples of heart rate determination procedures that support techniques for heart rate detection in accordance with aspects of the present disclosure.
Figure 3:
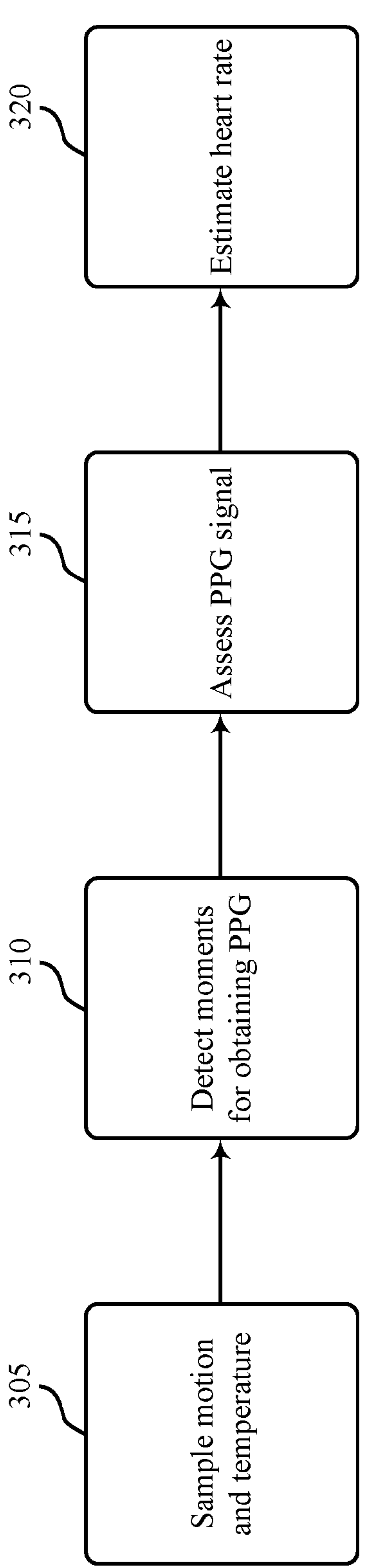

FIG. 3 illustrates an example of a heart rate determination procedure 300 that supports techniques for heart rate detection in accordance with aspects of the present disclosure. The heart rate determination procedure 300 may implement, or be implemented by, aspects of the system 100, system 200, or both. For example, in some implementations, the heart rate determination procedure 300 may result in heart rate data (e.g., daytime heart rate data, awake heart rate data) that may be displayed to a user via the GUI 275 of the user device 102, as shown in FIG. 2.

As will be described in further detail herein, the system 200 may be configured to estimate heart rate data 320 for a user based on the user's physiological and PPG data. As such, the heart rate determination procedure 300 illustrates a procedure for determining heart rate data of the user, such as daytime heart rate data, awake heart rate data, non-resting heart rate data, etc., based on physiological and PPG data of the user. Accordingly, a wearable device may detect heart rate of a user throughout the day, or throughout a duration that the user is awake, or throughout a duration the user is active (or not resting), or a combination thereof, in accordance with the heart rate determination procedure 300. For example, at 305, the system 200 may sample motion and temperature data of the user. Subsequently, at 310, the system 200 may detect moments for obtaining PPG based on the acquired motion and temperature data. At 315, and based on detecting moments for obtaining PPG, the system 200 may sample PPG and assess the PPG signal. At 320, and based on the signal quality of the PPG signal, the system 200 may estimate the heart rate of the user. In some cases, the system 200 may determine, or estimate, heart rate data for a user based on heart rate data and/or PPG data for the user collected via the ring 104. In other cases, the ring 104 may determine or estimate the heart rate date for the user via other sensors, such as accelerometers, temperature sensors, LEDs (e.g., infrared LEDs, green LEDs, red LEDs, yellow LEDs).

At 305, a wearable device (e.g., the system 200, an element of system 200, such as a ring 104 or user device 106), may sample motion data, temperature data, or both of a user. For example, the wearable device may include one or more temperature sensors (e.g., temperature sensors 240 as depicted in FIG. 2), that the wearable device may use to detect temperature data of the user. Specifically, the wearable device may obtain temperature data of the user's skin, body, etc. (e.g., rather than ambient temperature around the user). In parallel with obtaining temperature data (e.g., at the same time), or different times, the wearable device may obtain motion data associated with the user. For example, the wearable device may include one or more motion sensors (e.g., motion sensors 245 as depicted in FIG. 2), that the wearable device may use to detect motion data of the user. In some cases, the motion data may refer to acceleration data. In such cases, the motion sensors on the wearable device may refer to accelerometers (e.g., three-dimensional (3D) accelerometers) that are capable of detecting a user's acceleration.

At 310, a wearable device (e.g., the system 200, an element of system 200, such as a ring 104 or user device 106), may detect moments for obtaining PPG. In some cases, it may be advantageous for the wearable device to detect moments for obtaining PPG, rather than obtaining PPG continuously. For example, by obtaining PPG over a set of discrete moments, rather than continuously, the wearable device may mitigate power consumption, conserve battery power, etc. As the wearable device may be constrained to obtaining a PPG signal during a set of moments, the wearable device may be configured to detect moments in which the PPG signal may meet a quality threshold, so as to ensure that the wearable device obtains quality PPG data.

For example, detecting the suitable moments may be based on an amount of time (e.g., amount of time since a most recent heart rate measurement), based on physiological data of the user (e.g., temperature data, motion data), or a combination thereof. In some cases, the wearable device may determine or be configured with conditions such as an interval of time for detecting the PPG moments (e.g., moments to start obtaining PPG). For example, the wearable device may determine or otherwise be configured with an interval of X minutes. In some cases, the wearable device may detect the PPG moments to be every X minutes in accordance with the interval. It should be understood that the interval may not be limited to minutes and may instead be in units of milliseconds, seconds, hours, etc. In some cases, the wearable device may detect the PPG moments based on a set of conditions, such as based on a time interval and physiological data of the user. In some cases, the wearable device may detect a PPG moment based on reaching the end of the interval (e.g., after X minutes have elapsed) and based on one or more physiological conditions meeting a quality threshold. For example, every X minutes (e.g., in accordance with the interval) the wearable device may determine if one or more physiological conditions meet a quality threshold. If the one or more physiological conditions do meet the quality threshold, then the wearable device may detect the end of that interval as a moment for obtaining PPG. If the one or more physiological conditions do not meet the quality threshold, then the wearable device may determine not to obtain PPG at the end of that interval. In either case, after another X minutes (or other suitable period or interval of time), the wearable device may again determine whether the one or more physiological conditions meet the threshold in order to detect a PPG moment, and so on. In some cases, the interval, X, may be equal to five minutes.

In some cases, the wearable device may be configured with a maximum amount of time the wearable device may wait in between PPG measurements. For example, the wearable device may determine or otherwise be configured with a maximum time equal to Y minutes, where Y is greater than X. Accordingly, if the wearable device has not detected a moment for obtaining PPG in Y minutes, then the wearable device may determine to obtain PPG (e.g., regardless of the physiological condition quality). In some cases, the maximum time, Y, may be equal to ten minutes. In such cases, the system 200 may be configured to sample PPG and/or determine a heart rate measurement for the user at least every ten minutes. It should be understood that the maximum time, Y, may not be limited to minutes and may instead be in units of milliseconds, seconds, hours, etc. In some cases, the wearable device may determine to obtain PPG at all times (e.g., continuously).

The wearable device may obtain PPG based on the detected moments. The wearable device may obtain PPG data via a PPG system (e.g., PPG system 235). For example, the wearable device may start sampling PPG at the beginning of the detected moment and may continue obtaining the PPG for a duration of Z minutes. In some cases, the wearable device may determine, receive an indication, or identify a preconfiguration of the duration for obtaining PPG. For example, the duration of Z or an indication to stop PPG sampling may be determined by physiological signals (e.g., motion or temperature), or may be a variably determined based on an obtained number of heart rate values meeting a quality threshold. In some cases, the Z minute duration may be associated with the X minute interval. For example, the Z minute duration may be less than the X minute interval. In some cases, the PPG duration, Z, may be equal to one minute (e.g., system 200 samples PPG for one minute). It should be understood that the PPG duration, Z, may not be limited to minutes and may instead be in units of milliseconds, seconds, hours, etc.

At 315, a wearable device (e.g., the system 200, an element of system 200, such as a ring 104 or user device 106), may assess the PPG signal obtained during the detected moments. In some cases, assessing the PPG signal may include determining a quality of the PPG signal. In some cases, the wearable device may determine whether the PPG signal at least meets a quality threshold. In some cases, the wearable device may determine whether to use the PPG signal to determine heart rate based on the PPG signal satisfying the threshold. In some cases, the wearable device may determine whether portions of the PPG signal satisfy a quality threshold. The wearable device may use portions of the PPG signal that satisfy the quality threshold for determining heart rate.

In some implementations, the wearable device 105 may select a channel (e.g., a set of one or more sensors) for collecting the PPG data. For example, the wearable device 104 may be configured with multiple PPG sensors, where a PPG sensor may be an emitter (e.g., LED) and receiver (e.g., photodetector) pair which make up an optical path (e.g., channel) for PPG measurement. In some cases, a PPG sensor may refer to one or more green LEDs, one or more red LEDs, one or more IR LEDs, or any other set of LEDs and may select one or more PPG sensors for obtaining the PPG data based on a signal quality associated with one or more of the PPG sensors. For example, the wearable device may select a set of one or more PPG sensors for sampling PPG data based on the set of one or more PPG sensors being associated with a highest signal quality and/or satisfying a signal quality threshold.

At 320, a wearable device (e.g., the system 200, an element of system 200, such as a ring 104 or user device 106), may estimate heart rate of the user based on the obtained PPG signal. Each time that a user's heart beats, blood is pumped out to the arteries located in the hands and fingers. PPG sensors (e.g., of the PPG system 235 as described with reference to FIG. 2) in the wearable device are able to detect these changes in blood flow and volume using light reflection and absorption. Each pulse causes the arteries in the finger to alternate between swelling and contracting. By shining a light on the skin, such as via LEDs, changes in light reflected back from the wavering volume of red blood cells in the arteries are accounted for. From here, PPG can represent these blood flow changes through a visual waveform that represents the activity of the user's heart, and thus heart rate. In some cases, the wearable device may determine the heart rate of the user based on the PPG signal satisfying a quality threshold, or based on portions of the PPG signal satisfying a quality threshold. For example, the wearable device may determine one or more portions of the PPG signal that accurately represent the heart rate of the user.

A wearable device may be configured to perform all or a subset of the heart rate determination procedure 300 to determine heart rate data of a user. In some cases, the wearable device may obtain daytime heart rate data, awake heart rate data, heart rate data irrespective of whether the user is resting, or any combination thereof. Accordingly, a wearable device may perform one or more steps of the heart rate determination procedure 300 based on a time of day, such as being within a time range of a 24-hour window, based on the user being awake, etc. In some cases, the wearable device may perform one or more steps of the heart rate determination procedure 300 to obtain heart rate data of a user at all times (e.g., irrespective of time of day, whether the user is awake). Additionally, or alternatively, the respective steps and procedures of the heart rate determination procedure 300 may be performed by any of the respective components of the system 200, such as the ring 104, user device 106, servers 110, or any combination thereof.

Figure 4:
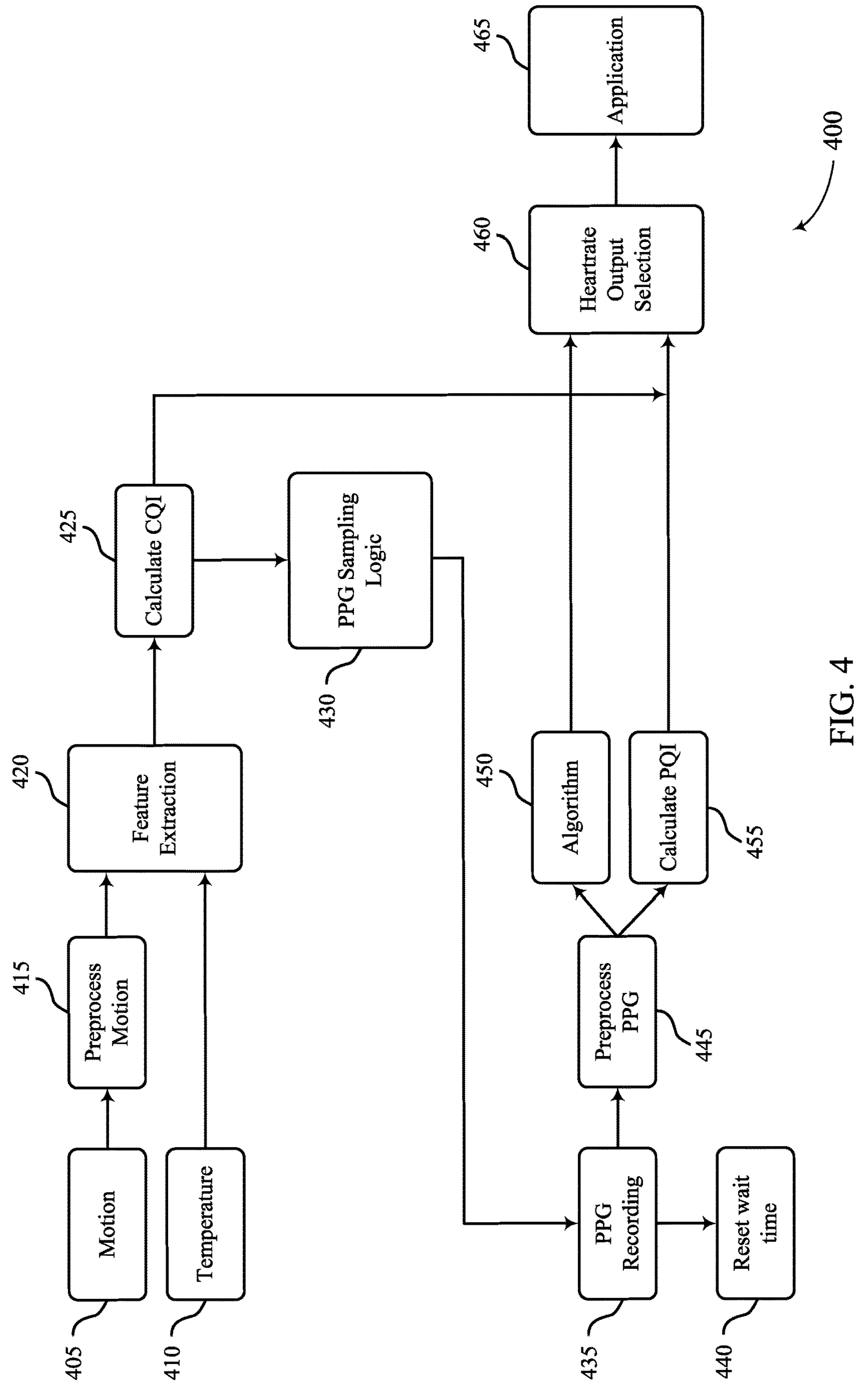

FIG. 4 illustrates an example of a heart rate determination procedure 400 that supports techniques for heart rate detection in accordance with aspects of the present disclosure. The heart rate determination procedure 400 may implement, or be implemented by, aspects of the system 100, system 200, heart rate determination procedure 300, or a combination thereof. For example, in some implementations, the heart rate determination procedure 400 may result in heart rate data (e.g., daytime heart rate data, awake heart rate data) that may be displayed to a user via the GUI 275 of the user device 102, as shown in FIG. 2. In some cases, heart rate determination procedure 400 may be related to all or a portion of heart rate determination procedure 300, or vice versa.

As described herein, a system, such a system 200, or a portion of system 200, such as a wearable device (e.g., a ring 104), may determine a heart rate of a user based on a set of conditions, where the conditions may refer to one or more thresholds, physiological data, PPG data, or a combination thereof. In some cases, a wearable device may detect heart rate of a user throughout the day, throughout a duration that the user is awake, throughout a duration the user is active (or not resting), or a combination thereof, in accordance with the heart rate determination procedure 400.

At 405, the wearable device may measure motion data associated with the user. In some cases, the wearable device may measure motion data constantly, or periodically (e.g., in accordance with a periodicity). In some cases, the wearable device may measure motion for a configured duration, where the wearable device may be configured with or receive an indication of the configured duration or may determine the configured duration. To measure motion data, the wearable device may utilize one or more motion sensors on the wearable device (e.g., motion sensors 245). In some cases, the motion data may refer to acceleration data. In such cases, the motion sensors on the wearable device may refer to accelerometers (e.g., 3D accelerometers) that are capable of detecting a user's acceleration, such as 3D acceleration. In some cases, the accelerometers may measure the user's acceleration as 50 Hz, or some other frequency.

At 410, the wearable device may measure temperature data associated with the user. In some cases, the wearable device may measure temperature data constantly, or periodically (e.g., in accordance with a periodicity). In some cases, the wearable device may measure temperature for a configured duration, where the wearable device may be configured with or receive an indication of the configured duration or may determine the configured duration. For example, the wearable device may measure the temperature of the user once per minute (1 temperature measurement/min). To measure temperature data, the wearable device may utilize one or more temperature sensors on the wearable device (e.g., temperature sensors 240).

At 415, the wearable device may preprocess the motion data. For example, the wearable device may preprocess the 3D acceleration data (e.g., raw data) to obtain processed acceleration data. In some cases, one or more of steps 405, 410, and 415 may be performed in parallel. For example, the wearable device may obtain temperature data and motion data in parallel, and preprocess the motion data subsequently. In some cases, the wearable device may obtain motion data and process the motion data in parallel with obtaining temperature data.

At 420, upon preprocessing the motion data, the preprocessed motion data and temperature data are input into a feature extraction module. The feature extraction module may determine one or more characteristics of the temperature data, preprocessed motion data, or a combination thereof. For example, the feature extraction module may determine a standard deviation, variance, range, average, etc., of the temperature data, preprocessed motion data, or a combination thereof. In some cases, the feature extraction module may determine the one or more characteristics for a window of time of the obtained data, such as a three second window. The wearable device may be configured with or determine the window of time to use for determining the characteristics.

At 425, the wearable device may calculate a condition quality index (CQI) associated with the temperature data, motion data, or a combination thereof. To calculate CQI, the wearable device may use the temperature data, preprocessed motion data, one or more characteristics of the data (e.g., the one or more characteristics determined at 420), or a combination thereof. In some aspects, the CQI metrics may indicate a relative quality of physiological data collected throughout a given time interval for determination of heart rate measurements. In other words, a CQI metric for a given time interval may indicate whether or not physiological data collected within the respective time interval is good for performing heart rate measurements. In some cases, the wearable device may determine a single CQI to reflect the quality of the temperature data, and motion data. In some other cases, the wearable device may determine a CQI for motion data and a separate CQI for temperature data. In some cases, the wearable device may calculate CQI constantly, or in accordance with a periodicity. For example, the wearable device may calculate a CQI value every three seconds. The wearable device may use one or more CQI calculations as an indication of the quality of the temperature data, the motion data, or both, obtained by the wearable device.

In some aspects, the system 200 may input features that were determined at 420 into a classifier in order to generate the CQI metric(s). For example, the system 200 may input features into a classifier (e.g., machine learning classifier, neural network), where the classifier is configured to determine one or more CQI metrics based on the received features. For instance, the system 200 may determine an average motion and an average temperature at 420, and may input these features into a classifier, where the classifier determines a CQI metric based on the average motion and average temperature.

At 430, the wearable device may perform PPG sampling logic to determine whether to start PPG sampling. In some cases, the wearable device may be configured to minimize power consumption of the wearable device. Accordingly, the wearable device may limit PPG recording. The wearable device may determine whether to record PPG based on one or more conditions, such as a periodicity (e.g., wait time, interval), CQI, or a combination thereof. In some cases, the system 200 may determine whether or not to perform PPG sampling based on the CQI metric calculated at 425 satisfying (or failing to satisfy) some threshold metric value. For example, in some cases, the system 200 may determine a CQI metric based on features extracted at 425, including an average motion and an average temperature. In such cases, the system 200 may calculate a CQI metric and may determine that the CQI metric satisfies a threshold metric value based on the average motion being less than or equal to a motion threshold and the average temperature being greater than or equal to a temperature threshold.

In additional or alternative cases, the underlying condition for determining whether to start PPG may be a periodicity. For example, the wearable device may be configured to assess whether to start PPG every X minutes, such as every 5 minutes. In other words, the system 200 may evaluate whether or not to perform PPG sampling every 5 minutes. To assess whether to start PPG sampling at the X minute mark, the wearable device may assess the data being obtained by the wearable device, such as the temperature data, and motion data. For example, the wearable device may assess the data to ensure that the limited PPG data the wearable device does obtain is quality PPG data. Quality PPG data may be based on motion of the user, temperature of the user, position of the wearable device on the user, etc. For example, quality PPG data be obtained when the motion of the user is below a motion threshold, when the skin temperature of the user is greater than a temperature threshold, when the position of the wearable device on the user is such that the wearable device is obtaining accurate data (e.g., motion data, temperature data), or a combination thereof.

For example, the temperature data (e.g., skin temperature) may be associated with blood circulation, such as blood circulation of the part of the body that the wearable device resides (e.g., the fingers in the case that the wearable device is a ring 104). Ambient temperature, exercise, etc., may impact blood circulation. In some cases, blood circulation and temperature may be directly correlated, such that if blood circulation decreases, skin temperature may decrease. If skin temperature falls below a threshold, this may be an indication that the wearable device may be unable to accurately detect blood circulation and accordingly, may be unable to obtain an accurate pulse read. In some cases, the wearable device may be configured with or identify a baseline temperature of the user, or a baseline range of temperatures. The wearable device may compare temperature measurements (e.g., instantaneous temperature measurements) to the baseline temperature (or range). For example, the wearable device may compare the instantaneous temperature measurement to the lower threshold of a baseline range and if the instantaneous temperature falls below the lower threshold, then the instantaneous temperature may be too low to obtain accurate pulse data.

Accordingly, every X minutes, the wearable device may assess the temperature data, motion data, CQI, or a combination thereof. For example, if the amount of time passed since the last assessment (e.g., the wait time) is greater than or equal to X minutes, and the CQI is greater than or equal to a CQI threshold, then the wearable device may start recording PPG. However, if the CQI does not meet the CQI threshold, then the wearable device may not start recording (e.g., refrain from sampling PPG). In some cases, the CQI threshold may be equal to zero. Accordingly, the wearable device may use the CQI calculations to determine moments for obtaining PPG. In some cases, the wearable device may use a set of CQI calculations to determine whether to start sampling PPG. Accordingly, the wearable device may compare each CQI in the set to a CQI threshold, or compare an average CQI of the set to a CQI threshold, etc., to determine whether to start sampling PPG.

In some cases, the wearable device may be configured with a maximum amount of time that the wearable device can go without recording PPG and/or performing a heart rate measurement, such as Y minutes. Y may be greater than X. In some cases, Y may be equal to ten minutes. In other words, the system 200 may be configured to sample PPG and/or obtain a heart rate measurement for the user at least every ten minutes. For example, if the time from the last PPG recording (or last performed heart rate measurement) is greater than or equal to Y minutes, the wearable device may start recording PPG, regardless of CQI. Starting the PPG in accordance with reaching the Y minutes may be referred to as a forced measurement. In some cases, forced measurements may be treated differently than PPG measurements obtained at X minutes and based on CQI meeting the CQI threshold. For example, the forced measurements may be additionally assessed, compared to a quality threshold, weighted less than non-forced measurements, etc.

The wearable device may be configured to record PPG for a defined time interval, such as Z minutes. In some cases, Z may be equal to one minute. Accordingly, at 435, the wearable device may start the PPG recording in accordance with the PPG sampling logic for Z minutes. The wearable device may sample the PPG at a set of conditions, such as frequency (e.g., 50 Hz).

In some cases, the wearable device may sample PPG data for the user using one or more sets of PPG sensors, where each set of PPG sensors includes at least one LED and at least one photodetector. For example, a wearable device may include a first pair of PPG sensors including a first LED and a first photodetector, and a second pair of PPG sensors including a second LED and a second photodetector. In other words, the wearable device may include two separate "channels" for acquiring PPG data (e.g., two separate PPG signals from the two respective pairs of sensors). In some cases, the wearable device may sample PPG data using the first and second pairs of PPG sensors simultaneously. Additionally, or alternatively, the wearable device may sample PPG data using the first and second sets of PPG sensors sequentially. For instance, the wearable device may sequentially control an activation state of the first pair of PPG sensors and the second pair of PPG sensors (e.g., first pair is in an active state when the second pair is in an inactive state, and vice versa). Sequentially activating separate sets/pairs of PPG sensors may improve the quality and accuracy of each respective PPG signal, reduce interference, and may lead to more accurate heart rate measurements.

At 440, upon sampling PPG, the wearable device may reset the wait time such that in another X minutes, the wearable device can again assess PPG sampling logic. Subsequently, or in parallel, at 445, the wearable device may preprocess the PPG data. For example, the wearable device may filter the PPG data, such as to remove erroneous samples. In some cases, processing the PPG data may include selecting PPG data obtained from a certain sensor (e.g., a green LED, infrared LED, red LED, yellow LED) or pair of PPG sensors, averaging the PPG data obtained across multiple sensors, etc.

For example, in some cases, the wearable device may monitor PPG signals from multiple sets of sensors. For instance, the system 200 may determine a first PPG signal from a first set of PPG sensors and a second PPG signal from a second set of PPG sensors, where each respective set of PPG sensors includes at least one LED and at least one photodetector. In the context of a ring wearable device, each of the respective sensors used for PPG sampling (e.g., LEDs, photodetectors) may be positioned at a different radial position along an inner circumference of the ring. In this example, the first or second PPG signal from one or more of the multiple sets of PPG sensors may be more reliable than the PPG signals obtained from other of the multiple sensors, such as due to the positions of the sensors around the wearable device and in relation to the user, a relative quality of skin contact with each respective sensor or LED, and the like. For example, a sensor located on the underside (e.g., palm side) of a user's finger may result in more accurate PPG data than a sensor located over the bone of the finger (e.g., on the backhand side of the finger). By way of another example, a relative positioning of a wearable device may result in less skin contact at one first sensor as compared to a second sensor, and may therefore result in lower quality PPG data as compared to the second sensor.

Accordingly, in some cases, the wearable device may determine whether to obtain and/or utilize the PPG data collected from a certain sensor, or whether to combine the PPG data obtained across multiple sets of PPG sensors using various mathematical operations, such as an averaging operation, a weighted averaging operation, and the like. In other words, the system 200 may combine multiple PPG signals collected via multiple sets of PPG sensors in order to generate a "composite" PPG signal that will be used to determine heart rate measurements for the user.

In some implementations, and as described in more detail with reference to FIGS. 5 through 7, the wearable device 105 may select a channel (e.g., a set of one or more sensors) for collecting the PPG data based on signal quality, where the signal quality may be impacted based on a position of a PPG sensor on a user, an activity of the user, a temperature of the user, etc. For example, the wearable device may be configured with multiple PPG sensors, such as one or more green LEDs, one or more red LEDs, one or more IR LEDs, or any other set of LEDs and may select one or more PPG sensors for obtaining the PPG data based on a signal quality associated with one or more of the PPG sensors. For example, the wearable device may select a set of one or more PPG sensors for sampling PPG data based on the set of one or more PPG sensors being associated with a highest signal quality and/or satisfying a signal quality threshold.

In some cases, the signal quality criteria to be used for selecting a PPG sensor may be based on a use case. The signal quality criteria may be based on one or more parameters, where the one or more parameters may include an illness of the user (e.g., pneumonia), a disease of the user (e.g., apnea, AFib), a current workout, a previous workout, or a planned future workout, etc. For example, one or more of the parameters may be associated with a different type of signal, signal shape, etc., and thus, the signal quality criteria may change based on the one or more parameters. Therefore, the device may identify the one or more parameters (e.g., use cases) that apply, if any, and determine the signal quality criteria to use for selecting one or more PPG sensors.

The wearable device may select the channel in any combination with any of the steps described herein and/or in any order.

At 450, the wearable device may apply an algorithm to the PPG data. In some cases, the algorithm may be referred to as an S-pulse algorithm. In some cases, the algorithm may output one or more measurements, such as IBI values (e.g., ibiCorrected, ibiQuality, ibi, timestamps of the ibi values (tibi)).

At 455, and at the same time or at a different time relative to applying the algorithm to the PPG data at 450, the wearable device may calculate a PPG quality indicator (PQI) associated with the PPG data (e.g., PPG quality metric), where the PQI may provide an indication of the quality of the PPG data as a whole, or in parts. In other words, the PPG quality metric may indicate a relative quality of the sampled PPG data. In some cases, the system 200 may determine the PPG quality metric (e.g., PQI) by comparing PPG data sampled at 435 to other PPG data that has been previously collected for the same user, to PPG data collected from other users, or both. In other words, the system 200 may determine a relative quality of the sampled PPG data (e.g., PQI of the sampled PPG data) by comparing the sampled PPG data to baseline PPG data sampled from the user and/or other users.

At 460, one or more outputs of the algorithm determined at 450 (e.g., ibiQuality), CQI, and the PQI may be input to a heartrate output module. The wearable device may use the heartrate output module to select heart rate values for the user based on the PPG data satisfying a quality threshold. For example, the wearable device may remove erroneous heart rate data. In other words, the system 200 may be configured to determine a heart rate measurement for the user based on the PPG quality metric (e.g., PQI) satisfying a threshold PPG metric value. By evaluating the determined PPG quality metric with respect to some threshold PPG metric value, the system 200 may ensure that sampled PPG data may result in an accurate heart rate measurement. One or more aspects of heart rate output selection at 460 may be described in additional detail with reference to FIG. 8.

In some cases, and as described in more detail with reference to FIG. 8, selecting the heart rate values may be based on comparing heart rate data to a set of one or more thresholds so as to display the heart rate data based on a quality of the data. In some cases, determining the quality of the data may be performed in accordance with an iterative (e.g., tiered) comparison procedure. In some cases, each heart rate data point (or a series of heart rate data points) may be labeled to indicate a quality of the heart rate data point.

At 465, the time series of the heart rate data may be displayed in an application (e.g., a GUI 275). Presentation of heart rate data will be further shown and described with reference to FIG. 9 below.

In some cases, steps 405 through 455 may be performed by firmware of a wearable device, such as a ring 104. In some cases, the wearable device may communicate one or more results of steps 405 through 455 with a device associated with the wearable device, such as user device (e.g., user device 106). Step 460 may be performed by the wearable device, the user device, or a combination thereof. Step 465 may be performed by the wearable device, the user device, an application (e.g., an application on the user device), or a combination thereof.

Figure 5:
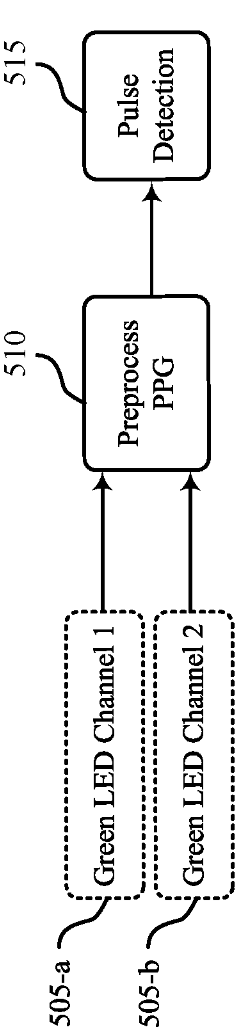

FIG. 5 illustrates an example of a channel selection procedure 500 that supports techniques for heart rate detection in accordance with aspects of the present disclosure. The channel selection procedure 500 may implement, or be implemented by, aspects of the system 100, system 200, heart rate determination procedures 300 and 400, or a combination thereof. For example, in some implementations, the channel selection procedure 500 may result in selection of one or more PPG sensors to use for sampling PPG data, where the PPG data may be used to determine heart rate data (e.g., daytime heart rate data, awake heart rate data) that may be displayed to a user via the GUI 275 of the user device 102, as shown in FIG. 2. In some cases, channel selection procedure 500 may be related to all or a portion of heart rate determination procedures 300 or 400, or vice versa. For example, channel selection procedure 500 may be implemented in steps 430 and/or 435 as described with reference to FIG. 4.

As described herein, a wearable device may sample PPG data for determining heart rate data of a user using one or more PPG sensors (e.g., channels, LEDs). For example, in some cases, wearable device may be configured to obtain PPG data via one or more PPG sensors. For example, the wearable device may be configured to obtain PPG data use a same PPG sensor or a same set of PPG sensors to obtain PPG data each time heart rate is measured. For example, the wearable device may be configured to sample PPG data using a green LED and photodetector pair, such as green LED channel 1 at 505-*a* (e.g., GRE1 PD1) including a first green LED and a first photodetector, or green LED channel 2 at 505-*b* (e.g., GRE2 PD2) including a second green LED and a second photodetector, or a combination thereof. In some cases, the wearable device may be configured to utilize one or more green LEDs to obtain PPG data. In particular, green LEDs may result in the most accurate data (as compared to other LED types) in certain conditions (e.g., ideal conditions).

In some cases, however, the performance of the one or more PPG sensors configured for obtaining PPG data (e.g., green LEDs) may decrease and/or fall below a threshold. Additionally or alternatively, one or more other sensors of the wearable device (e.g., red LEDs, IR LEDs, other colored LEDs such as yellow LEDs) may perform the same or better than the green LEDs. For example, in some cases, signal quality of a first PPG sensor may be impacted by environmental parameters more so than a second PPG sensor. Environmental parameters may include ring rotation, ring fit (e.g., which may change over time such as over the course of a day, and/or over the course of months, years, etc.), condition of the wearable device and/or sensors of the wearable device (e.g., a new device may perform differently than an older device), temperature of the user's skin, ambient temperature, etc. For example, in ideal conditions (e.g., low movement, warm skin temperature, the PPG sensor is positioned on the palm side of a user's finger), a green LED may result in more accurate PPG data than an IR LED.

However, in less than ideal conditions or as conditions change, the green LED may not perform as well as an IR LED (e.g., the IR LED may be more robust, substantial, etc.). For example, IR diodes may exhibit superior performance as compared to green LEDs in cases of high movement (e.g., during exercise) and/or in cases of cold skin temperatures. Additionally or alternatively, some PPG sensors may be more bothersome to the user than other PPG sensors. For example, when in use, LEDs that utilize the visible light spectrum (e.g., green LEDs) may be visible to the user, whereas LEDs that do not utilize the visible light spectrum (e.g., IR LEDs) may not be visible to the user.

Accordingly, it may be beneficial to allow the wearable device to flexibly switch between sensors and/or sensor types (e.g., green LEDs versus IR LEDs versus red LEDs, etc.) for sampling PPG data used for heart rate measurement. For example, the wearable device may select one or more sensors for obtaining the PPG data used for heart rate measurement based on a signal quality associated with one or more of the sensors. The signal quality threshold may be a number of pulses detected per a time interval, a PPG quality index, some other signal quality index, etc. For example, the wearable device may select a set of one or more sensors for sampling PPG data based on the set of one or more sensors being associated with a highest signal quality and/or satisfying a signal quality threshold. Accordingly, the wearable device may obtain PPG data with increased quality and reliability. Upon selecting a set of one or more PPG sensors, the wearable device sample PPG data, process the PPG (at 510), and perform pulse detection (515), as described in more detail herein.

Figure 6:
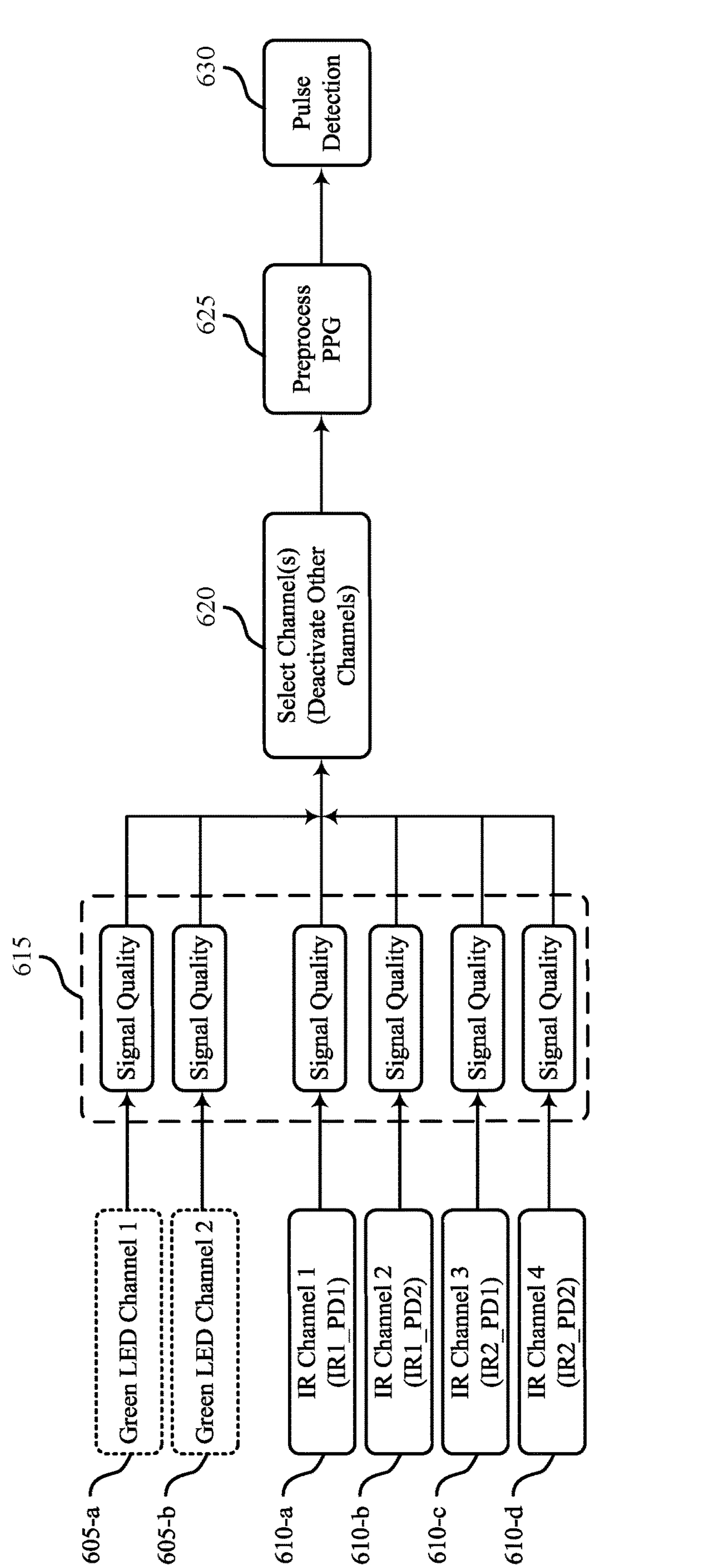

FIG. 6 illustrates an example of a channel selection procedure 600 that supports techniques for heart rate detection in accordance with aspects of the present disclosure. The channel selection procedure 600 may implement, or be implemented by, aspects of the system 100, system 200, heart rate determination procedures 300 and 400, channel selection procedure 500, or a combination thereof. For example, in some implementations, the channel selection procedure 600 may result in selection of one or more PPG sensors to use for sampling PPG data, where the PPG data may be used to determine heart rate data (e.g., daytime heart rate data, awake heart rate data) that may be displayed to a user via the GUI 275 of the user device 102, as shown in FIG. 2. In some cases, channel selection procedure 600 may be related to all or a portion of heart rate determination procedures 300 or 400, or vice versa. For example, channel selection procedure 600 may be implemented in steps 430 and/or 435 as described with reference to FIG. 4.

As described herein, the procedure for determining heart rate may include selecting a channel for sampling the PPG data (e.g., a sensor capable of obtaining PPG data). For example, the wearable device may be configured with multiple PPG sensors, such as one or more green LEDs (e.g., green LED channels 1 and 2), one or more red LEDs, one or more IR LEDs (e.g., IR LED channels 1 through 4), or any other set of LEDs (e.g., other colored LEDs, such as yellow LEDs). For example, the wearable device may include any number of IR LEDs, such as two, and any number of photodetectors, such as two, where a combination of an IR LED and a photodetector may be referred to as a channel. Accordingly, IR channel 1 may correspond to a first IR LED and a first photodetector (e.g., IR1_PD1), IR channel 2 may correspond to the first IR LED and a second photodetector (e.g., IR1_PD2), IR channel 3 may correspond to a second IR LED and the first photodetector (e.g., IR2_PD1), and IR channel 4 may correspond to the second IR LED and the second photodetector (e.g., IR2_PD2).

Similarly, the wearable device may include any number of green LEDs, such as one, and any number of photodetectors, such as one, where a combination of a green LED and a photodetector may be referred to as a channel. In some cases, the green LED and photodetector pair may not be interchangeable. Accordingly, green LED channel 1 may correspond to a first green LED and a first photodetector (e.g., GRE1_PD1), and Green LED channel 2 may correspond to the second green LED and a second photodetector (e.g., GRE2_PD2). In some cases, the wearable device may be configured to select one or more PPG sensors for obtaining the PPG data based on a signal quality associated with the one or more of the PPG sensors. In other words, the wearable device may be configured to select which channel will be used to collect PPG data that will be used for heart rate measurement.

For example, the wearable device may be configured to analyze a set of one or more PPG sensors (e.g., a subset or all of the PPG sensors configured to the wearable device). For example, the wearable device may obtain data from the one or more PPG sensors. In some cases, and as described with reference to FIG. 2, the wearable device may obtain PPG data from the one or more sensors based on a set of conditions (e.g., a minim wait time, a maximum wait time, a quality metric, a sampling duration), where the set of conditions may be the same for each of the one or more PPG sensors, or different across the one or more PPG sensors. For example, the wearable device may start PPG sampling at each PPG sensor of the one or more PPG sensors if a minimum wait time since the last sampling is reached, and if a CQI is greater than a threshold. Additionally, or alternatively, the wearable device may start PPG sampling at each PPG sensor of the one or more PPG sensors if the maximum wait time since the last sampling is reached (regardless of CQI). In some cases, the wearable device may be configured to sample PPG data at each of the one or more PPG sensors in accordance with a sampling duration (e.g., one minute).

In some cases, the wearable device may be configured to sample the PPG data at 605-*a* and 605-*b* (e.g., corresponding to green LED channels 1 and 2, respectively) and/or be configured to sample the PPG data at 610-*a* through 610-*b* (e.g., corresponding to IR LED channels 1 through 4, receptively) in accordance with the set of conditions. For example, in some implementations, the wearable device may be configured so sequentially activate/deactivate each of the respective green and IR channels in order to sample the respective channels at each of 605-*a* through 610-*b*.

The wearable device may the perform a signal quality determination procedure at 615, in which the wearable device may determine (e.g., measure, calculate) a quality (e.g., a signal quality) of the output from each PPG sensor the wearable device sampled data from. For example, in the case that the wearable device sampled data at one or more of 605-*a* and 605-*b*, the wearable device may perform a signal quality determination for green LED channel 1 and green LED channel 2, respectively. In the case that the wearable device sampled data at one or more of 610-*a* through 610-*d*, the wearable device may perform a signal quality determination for IR LED channel 1 through IR LED channel 4. In some cases, the wearable device may sample data at all or some combination of 605-*a*, 605-*b*, 610-*a*, 610-*b*, 610-*c*, and 610-*d*.

In some cases, the wearable device may be configured to compare the signal quality of each PPG sensor to one or more signal quality thresholds and/or compare the signal quality of each PPG sensor to the other determined signal qualities. At 620, the wearable device may select one or more PPG sensors associated with the highest signal quality. For example, the wearable device may be configured to select the top N, sensors associated with the highest signal quality, where N may be any number greater than zero. Additionally, or alternatively, the wearable device may select the one or more PPG sensors that satisfy one or more signal quality thresholds. For example, the wearable deice may select a PPG sensor if the PPG sensor satisfies a signal quality threshold and the PPG sensor is associated with the highest signal quality. In another example, if the PPG sensor is associated with the highest signal quality but fails to satisfy the signal quality threshold, the wearable device may refrain from selecting a PPG sensor (e.g., refrain from performing a heart rate measurement).

In some cases, at 620, the wearable device may deactivate one or more PPG sensors, such as any PPG sensors that the wearable device did not activate. In other words, the wearable device may deactivate PPG sensors/channels that will not be used for PPG collection and heart rate detection. Deactivating the one or more PPG sensors may include turning the one or more sensors off, transitioning the one or more sensors in a stand-by condition, etc. Deactivating the one or more sensors may allow for power saving at the wearable device and may reduce user disturbance with regard to visible light that may have been caused by the one or more sensors remaining active. In some cases, the wearable device may be configured to re-activate the one or more deactivated PPG sensors, and/or the one or more deactivated sensors may be configured to re-activate themselves in accordance with a timer, for other non-PPG related purposes, etc.

In some implementations, the wearable device (and/or other components of system 200) may perform the PPG channel selection procedure illustrated in FIG. 6 each time heart rate data is to be collected. Moreover, in some implementations, the wearable device may be configured to implement a "feedback loop" to re-evaluate channel qualities even after a channel is selected. For example, the wearable device may originally select green LED channel 1, and utilize green LED channel 1 to collect PPG data that will be used for heart rate measurements. However, in this example, conditions may change such that green LED channel 1 subsequently exhibits poor signal quality. In such cases, the wearable device may be configured to re-measure all or a subset of the channels at 605-*a*, 605-*b*, 610-*a*, 610-*b*, 610-*c*, and/or 610-*d* to re-evaluate which channel should be used for heart rate measurements.

Accordingly, the wearable device may obtain PPG data with increased quality and reliability. Upon selecting a set of one or more PPG sensors, the wearable device may sample PPG data, process the PPG data (at 625), and perform pulse detection (630), as described in more detail herein.

FIG. 7 illustrates an example of a channel selection procedure 700 that supports techniques for heart rate detection in accordance with aspects of the present disclosure. The channel selection procedure 700 may implement, or be implemented by, aspects of the system 100, system 200, heart rate determination procedures 300 and 400, channel selection procedures 500 and 600, or a combination thereof. For example, in some implementations, the channel selection procedure 700 may result in selection of one or more PPG sensors to use for sampling PPG data, where the PPG data may be used to determine heart rate data (e.g., daytime heart rate data, awake heart rate data) that may be displayed to a user via the GUI 275 of the user device 102, as shown in FIG. 2. In some cases, channel selection procedure 700 may be related to all or a portion of heart rate determination procedures 300 or 400, or vice versa. For example, channel selection procedure 700 may be implemented in steps 430 and/or 435 as described with reference to FIG. 4.

As described herein, a wearable device may be configured to select one or more PPG sensors (e.g., channels) for obtaining PPG data based on signal quality. In some cases, the wearable device may include any number of IR LEDs, such as two, and any number of photodetectors, such as two, where a combination of an IR LED and a photodetector may be referred to as a channel. Accordingly, IR channel 1 may correspond to a first IR LED and a first photodetector (e.g., IR1_PD1), IR channel 2 may correspond to the first IR LED and a second photodetector (e.g., IR1_PD2), IR channel 3 may correspond to a second IR LED and the first photodetector (e.g., IR2_PD1), and IR channel 4 may correspond to the second IR LED and the second photodetector (e.g., IR2_PD2). Similarly, the wearable device may include any number of green LEDs, such as one, and any number of photodetectors, such as one, where a combination of a green LED and a photodetector may be referred to as a channel. In some cases, the green LED and photodetector pair may not be interchangeable. Accordingly, green LED channel 1 may correspond to a first green LED and a first photodetector (e.g., GRE1_PD1), and Green LED channel 2 may correspond to the second green LED and a second photodetector (e.g., GRE2_PD2).

The wearable device may be configured to analyze a set of one or more PPG channels (e.g., a subset or all of the PPG sensors configured to the wearable device). For example, the wearable device may obtain data from the one or more PPG sensors. In some cases, the wearable device may be configured with a default PPG sensor (e.g., a particular PPG sensor) or a default PPG sensor type (e.g., one or more IR LEDs, one or more green LEDS, etc.) to use for sampling PPG data. For example, the wearable device may be configured to use one or more IR sensors as a default, such as IR LED channels 1 through 4, for PPG sampling as long as the one or more IR sensors satisfy a signal quality threshold.

Accordingly, the wearable device may sample PPG data from the one or more IR channels at 705-*a*, 705-*b*, 705-*c*, and 705-*d*. At 710, the wearable device may determine a signal quality for each of IR channel 1 through 4. In some cases, the wearable device may be configured to compare the signal quality of each IR sensor to one or more signal quality thresholds and/or compare the signal quality of each IR sensor to the signal qualities of the other IR sensors. For example, at 715, the wearable device may determine if one or more of the IR channels 1 through 4 satisfies a signal quality greater than a threshold. If so, then the wearable device may select one or more of the IR channels for obtaining PPG data. The wearable device may select one or more IR channels if the IR channels satisfy the signal quality threshold. In some cases, the wearable device may select one or more IR channels associated with the highest signal quality. For example, the wearable device may be configured to select the top N number of IR sensors associated with the highest signal quality, where N may be any number greater than zero. For example, the wearable deice may select an IR sensor if the IR sensor satisfies a signal quality threshold and the IR sensor is associated with the highest signal quality. Upon selecting one or IR sensors, the wearable device may sample PPG data, process the PPG data (at 720), and perform pulse detection (725), as described in more detail herein.

If none of IR channels 1 through 4 satisfy the signal quality threshold, then the wearable device may analyze one or more other channels, such as green LED channels 1 and 2. In some cases, the wearable device may first activate the one or more other channels and sample PPG data from the one or more other channels. For example, all other channels other than the default channels (e.g., IR channels) may be deactivated and/or refrain from sampling data during steps 705 through 710. Accordingly, the wearable device may sample PPG data via green LED channel 1 at 730-*a* and green LED channel 2 at 730-*b*. At 735, the wearable device may determine a signal quality associated with each of the green LED channels 1 and 2. At 740, the wearable device may be configured to select the top N number of green LED channels associated with the highest signal quality, where N may be any number greater than zero. For example, the wearable deice may select a green LED sensor associated with the highest signal quality.

Additionally, or alternatively, in some cases, the wearable device may compare one or more of the green LED channels to a signal quality threshold. In some cases, the wearable device may use one or more of the green LED channels based on the one or more green LED channels satisfying the threshold. In some cases, if multiple green LED channels satisfy the quality threshold, the wearable device may select one or more green LED channels based on highest signal quality, for example. In some cases, if none of the green LED channels satisfy the quality threshold, the wearable device may continue to use one or more of the green LED channels. In some cases, if none of the green LED channels satisfy the quality threshold, the wearable device may restart the channel selection procedure at 705.

In some cases, upon determining that none of IR channels 1 through 4 satisfy the signal quality threshold, the wearable device may deactivate one or more of the IR channel. Deactivating the one or more IR channels may include turning the one or more IR sensors off, transitioning the one or more IR sensors in a stand-by condition, etc. In some cases, the wearable device may be configured to re-activate the one or more deactivated IR sensors, and/or the one or more deactivated IR sensors may be configured to re-activate themselves in accordance with a timer, for other non-PPG related purposes, etc.

As noted previously herein, the wearable device (and/or other components of system 200) may perform the PPG channel selection procedure illustrated in FIG. 6 each time heart rate data is to be collected. Moreover, in some implementations, the wearable device may be configured to implement a "feedback loop" to re-evaluate channel qualities even after a channel is selected. For example, the wearable device may originally select IR channel 1, and utilize IR channel 1 to collect PPG data that will be used for heart rate measurements. However, in this example, conditions may change such that IR channel 1 subsequently exhibits poor signal quality. In such cases, the wearable device may be configured to re-measure all or a subset of the IR channels at 705-*a*, 705-*b*, 705-*c*, and/or 705-*d* to re-evaluate which channel should be used for heart rate measurements. By way of another example, upon determining that the IR channel 1 exhibits poor signal quality, the wearable device may return to measure green LED channels at 730-*a*, and/or 730-*b* to determine whether green LED channels may exhibit better signal quality (and therefore more accurate heart rate measurements) as compared to IR channels.

Accordingly, the wearable device may obtain PPG data with increased quality and reliability. Upon selecting a set of one or more PPG sensors (e.g., IR sensors, or green LED sensors), the wearable device may sample PPG data, process the PPG data (at 720), and perform pulse detection (725), as described in more detail herein.

In some implementations, with reference to the channel selection procedures as described with reference to FIGS. 5 through 7, upon selecting one or more PPG sensors, conditions may change. Accordingly, the wearable device may be configured to perform all or a subset of one or more of the channel selection procedures (e.g., a feedback loop) to ensure signal quality.

As noted previously herein, in some cases, the signal quality criteria (e.g., signal quality thresholds) used for selecting a PPG sensor may be based on one or more use cases, such as an illness of the user (e.g., pneumonia), a disease of the user (e.g., apnea, AFib), a current workout, a previous workout, or a planned future workout, etc. In this regard, the signal quality thresholds used throughout the channel selection procedure 700 may be selected/adjusted based on one or more use cases or parameters associated with the user, where the use cases, parameters/characteristics, or both, may be determined based on collected physiological data, input by the user (e.g., via a GUI of a user device), or both.

Figure 8:
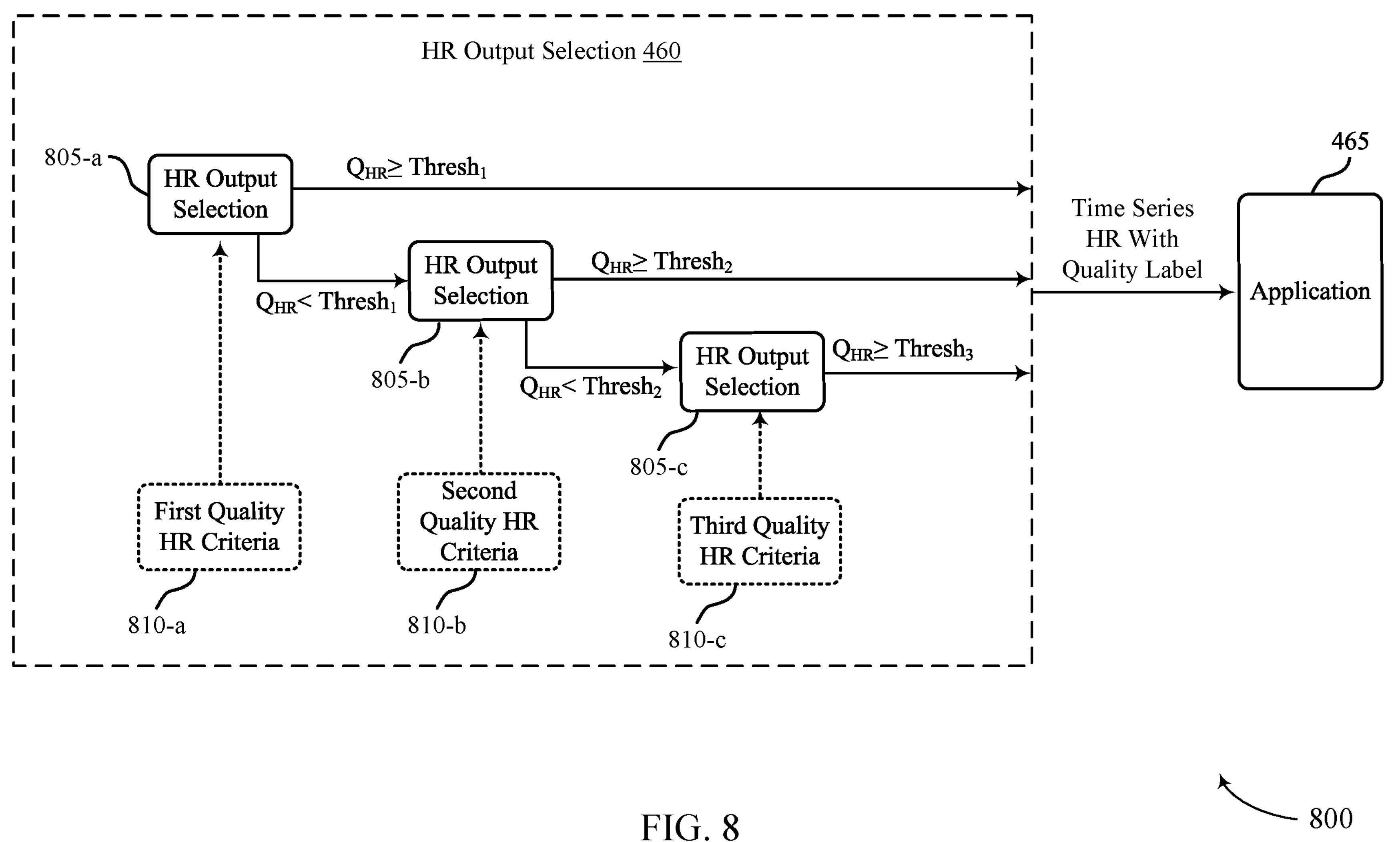
FIG. 8 illustrates an example of a heart rate determination procedure that supports techniques for heart rate detection in accordance with aspects of the present disclosure.

FIG. 8 illustrates an example of a heart rate determination procedure 800 that supports techniques for heart rate detection in accordance with aspects of the present disclosure. The heart rate determination procedure 800 may implement, or be implemented by, aspects of the system 100, system 200, heart rate determination procedures 300 and 400, channel selection procedures 500, 600, and 700, or a combination thereof. For example, in some implementations, the heart rate determination procedure 800 may result in heart rate data (e.g., daytime heart rate data, awake heart rate data) that may be displayed to a user via the GUI 275 of the user device 106, as shown in FIG. 2. In some cases, heart rate determination procedure 800 may be related to all or a portion of heart rate determination procedures 300 and 400, or vice versa. for example, heart rate determination procedure 800 may include heart rate determination procedure 400 as described with reference to FIG. 4.

As described herein, a wearable device may utilize PPG data to determine heart rate data of a user. Quality of heart rate data may be based on signal quality from one or more sensors of the wearable device which may be impacted by ring rotation, ring fit (e.g., which may change over time such as over the course of a day, and/or over the course of months, years, etc.), condition of the wearable device and/or sensors of the wearable device (e.g., a new device may perform differently than an older device), temperature of the user's skin, ambient temperature, activity level of the user, etc. Accordingly, the wearable device may analyze heart rate data by comparing the heart rate data to a set of criteria (e.g., thresholds). In some cases, the wearable device may determine whether to output the determined heart rate data based on the analysis. For example, if the heart rate data satisfies the set of criteria (e.g., exhibits a sufficient quality), then the device may output the heart rate data to the user. In the case that the heart rate data fails to satisfy the heart rate criteria (e.g., exhibits insufficient quality), the device may refrain from outputting the heart rate data. In such cases, the output heart rate data may be accurate, but there may be gaps in the heart rate data (e.g., heart rate trend) as a result of the wearable device/system refraining from outputting heart rate data for certain time periods. Comparatively, in other cases, the wearable device may be configured to output all heart rate data, regardless of quality of the data which may result in outliers, inaccuracies, etc.

In some cases, to mitigate the occurrence of gaps in the output data, while maintaining reliability of the heart rate data, the wearable device may be configured with multiple sets of criteria (e.g., multiple threshold quality metrics), where a latter criteria is relaxed from a former criteria of the multiple sets. In other words, in cases where collected heart rate data does not satisfy a first criteria or first threshold quality metric, instead of simply discarding the heart rate data (which would result in "gaps" in the user's heart rate data trend), the system may compare the collected heart rate data to additional, less-stringent criteria/threshold quality metrics. If the heart rate data satisfies the additional, less-stringent/threshold quality metrics, the system may output the heart rate data for display to the user, thereby reducing (or preventing) gaps in the user's heart rate data.

For example, a first set of criteria (e.g., first quality heartrate criteria at 810-*a*, first threshold quality metric) may be associated with the strictest criteria, the second set of criteria (e.g., second quality heartrate criteria at 810-*b*, second threshold quality metric) may be less strict than the first set but stricter than a third set (e.g., third quality heartrate criteria at 810-*c*, third threshold quality metric), and so on. Accordingly, the wearable device (or other components of system 200) may first compare a heart rate output selection to the first set of criteria at 805-*a*, and if the output satisfies (e.g., equal to or less than the threshold) the first set of criteria (e.g., QHR≥Thresh1), the device may output the heart rate data. That is, if the heart rate data satisfies the first threshold quality metric, the heart rate data may be output for display to the user.

Comparatively, if the output fails to satisfy the first set of criteria (e.g., QHR<Thresh1), the device may then compare the heart rate data to the second set of criteria at 805-*b*, where the second heart rate criteria is less strict (e.g., relaxed) as compared to the first set of criteria. That is, if the heart rate data fails to satisfy the first threshold quality metric, the system may compare the heart rate data to a second threshold quality metric, where the second threshold quality metric is less than (e.g., less stringent than) the first threshold quality metric. The device may perform such a procedure, such as through comparison at 805-*c*, until the output satisfies a set of criterion, and/or until the device runs out of criteria (e.g., exhausts all threshold quality metrics) to compare the output to, whichever comes first.

In some cases, the device may label the outputted data with a quality label. For example, heart rate data that passed the second set of criteria (e.g., second threshold quality metric) but not the first set of criteria (e.g., first threshold quality metric) may not be as reliable as data that passed the first set of criteria, and so the device may label all data, the most reliable data (e.g., data that satisfies the first quality criteria), or any data that failed to pass the first criteria with a label indicative of the quality of the output data. As such, the device may provide heart rate data to the user without gaps, or with minimal gaps in the data.

In the case that the output fails to satisfy any of the criteria (e.g., first, second, or third quality heartrate criteria), the device may refrain from outputting the data. In some other cases, the device may output the data but provide a label indicative of the low reliability of the data.

Accordingly, the device may determine a time series of heart rate data with quality labels indicative of the reliability of a corresponding data point. The device may then display the time series with or without the labels in an application (e.g., a GUI 275), at 465.

Figure 9:
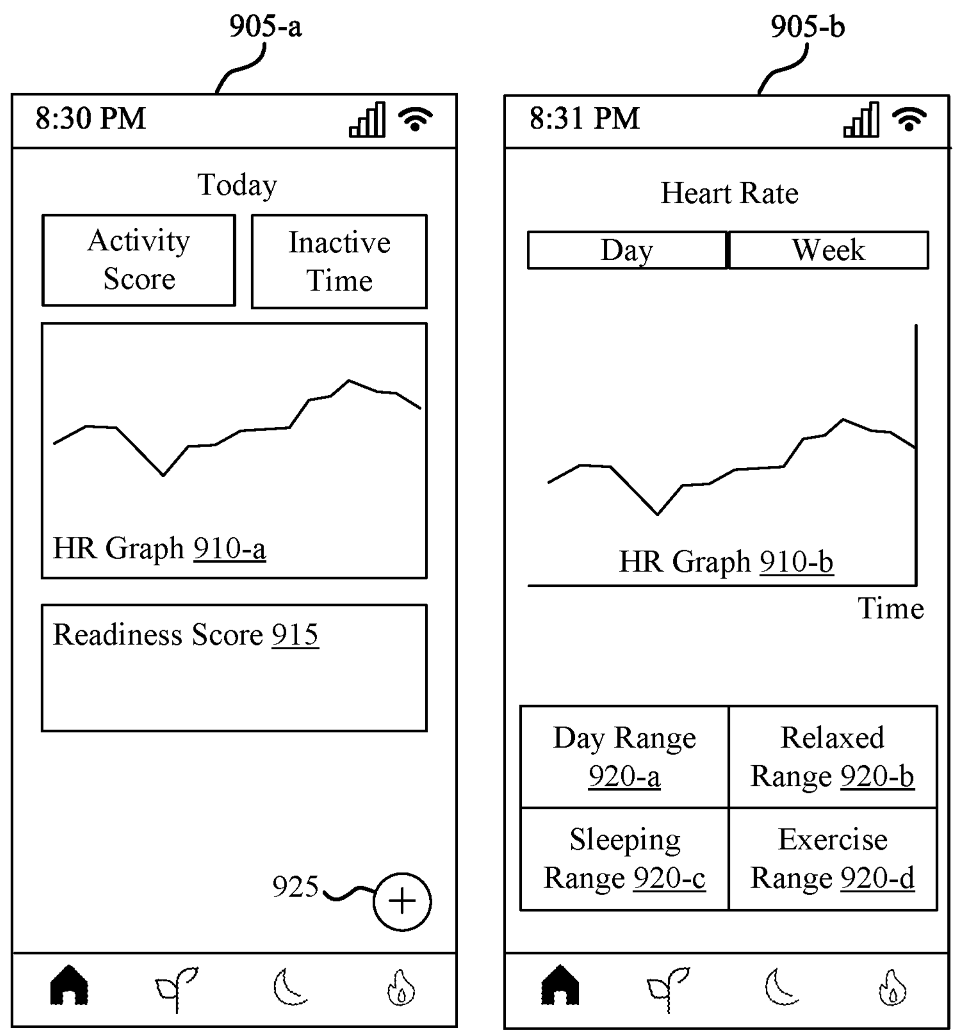
FIG. 9 illustrates an example of a graphical user interface (GUI) that supports techniques for heart rate detection in accordance with aspects of the present disclosure.

FIG. 9 illustrates an example of a GUI 900 that supports techniques for heart rate detection in accordance with aspects of the present disclosure. The GUI 900 may implement, or be implemented by, aspects of the system 100, system 200, heart rate determination procedure 300 and 400, channel selection procedure 500, 600, and 700, hear rate determination procedure 800, or any combination thereof.

For example, the GUI 900 may include an example of the GUI 275 included within the user device 106 illustrated in FIG. 2.

The GUI 900 illustrates a series of application pages 905 that may be displayed to the user via the GUI 900 (e.g., GUI 275 illustrated in FIG. 2). The server 110 of system 200 may cause the GUI 900 of the user device 106 (e.g., mobile device) to display an indication of the heart rate data (e.g., via application page 905-*a*, or 905-*b*). Accordingly, upon determining heart rate data (e.g., as described with reference to FIGS. 3 and 8), the user may be presented with the application page 905-*a* upon opening the wearable application 250. As shown in FIG. 9, the application page 905-*a* may display a heart rate graph 910-*a*. The heart rate graph 510-*a* may include a visual representation of how the user's heart rate reacted to different events and activities (e.g., exercise, sleep, rest, etc.). In some cases, the heart rate graph 910-*a* may display the heart rate of the user over minutes, hours, days, etc. In some cases, the heart rate graph 910 may display a combination of daytime heart rate data and nighttime heart rate data (e.g., awake heart rate data and asleep heart rate data). Additionally, in some implementations, the application page 905-*a* may display one or more scores (e.g., sleep score, readiness score 915, activity score, inactive time) for the user for the respective day (e.g., respective sleep day), where the one or more scores may be based on the heart rate data. By way of another example, the heart rate data may be used to update at least a subset of the factors for the readiness score 915 (e.g., subset of sleep, sleep balance, HRV balance, recovery index, activity, activity balance). In some cases, the user may select button 925 to add a workout, an unguided session, a tag, etc.

Continuing with reference to FIG. 9, a user may be able to select the heart rate graph 910-*a* on the application page 905-*a* in order to view details associated with the heart rate, as shown in application page 905-*b* ("heart rate modal"). In other words, tapping on the heart rate graph 910-*a* shown on application page 905-*a* may cause the GUI 900 to display application page 905-*b* so that the user may quickly and easily view the heart rate of the user over time. The application page 905-*b* may include a modal view including details for the heart rate. Heart rate graphs 910-*a* and 910-*b* may display the same or different graph. For example, the time scale may be the same or different. In some cases, application page 905-*b* may display a daytime heart rate graph (e.g., awake heart rate graph) and a nighttime heart rate graph (e.g., asleep heart rate graph) so as to allow a user to differentiate between the user's heart rate during the day (e.g., while awake and active) versus at night (e.g., while relaxed, sleeping). Application page 905-*b* may also include a day heart rate range 920-*a*, a relaxed heart rate range 920-*b*, a sleeping heart rate range 920-*c*, and an exercise heart rate range 920-*d*. The individual ranges may be on a per-hour basis, for example. In some cases, the application page 905-*b* may display the heart rate data as HRV, resting heart rate, etc.

The server of the system may cause the GUI 900 of the user device to display a message on application pages 905-*a*, 905-*b*, or both, associated with the identified heart rate data. The user device may display recommendations and/or information associated with the heart rate data via a message. In some implementations, the user device 106 and/or servers 110 may generate alerts (e.g., messages, insights) associated with the heart rate data which may be displayed to the user via the GUI 900 (e.g., application pages 905-*a*, or 905-*b*, or some other application page). In particular, the messages generated and displayed to the user via the GUI 900 may be associated with one or more characteristics (e.g., time of day, duration, range) of the heart rate data. For example, the message may alert the user to breathe, take a moment to relax, etc., based on the user's heart rate. In some cases, the message may display a recommendation of how to adjust their lifestyle to achieve a particular heart rate. In this regard, the system may be configured to display messages or insights to the user in order to facilitate effective, healthy patterns for the user.

Figure 10:
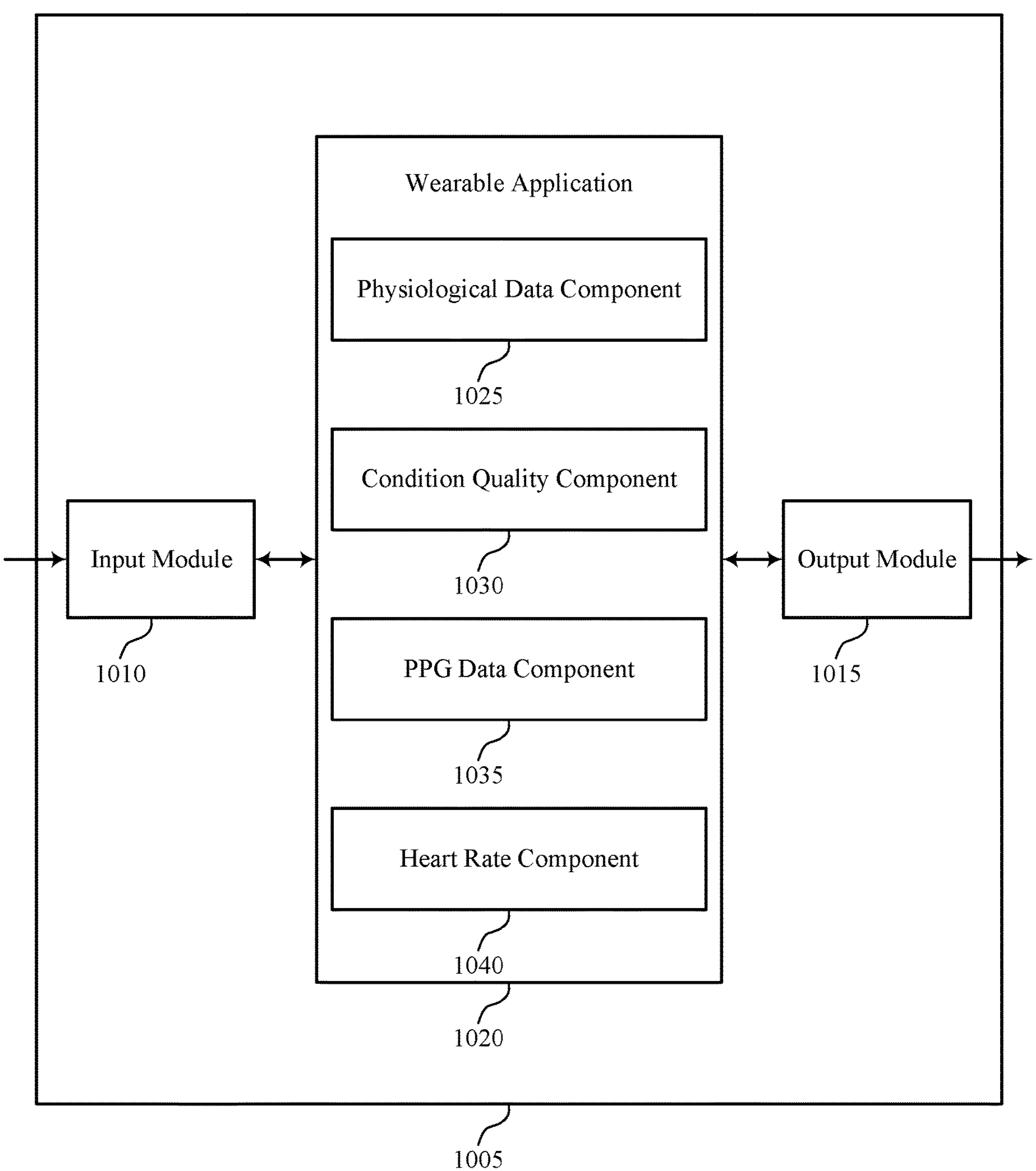
FIG. 10 shows a block diagram of an apparatus that supports techniques for heart rate detection in accordance with aspects of the present disclosure.

FIG. 10 shows a block diagram 1000 of a device 1005 that supports techniques for heart rate detection in accordance with aspects of the present disclosure. The device 1005 may include an input module 1010, an output module 1015, and a wearable application 1020. The device 1005 may also include a processor. Each of these components may be in communication with one another (e.g., via one or more buses).

The input module 1010 may provide a means for receiving information such as packets, user data, control information, or any combination thereof associated with various information channels (e.g., control channels, data channels, information channels related to illness detection techniques). Information may be passed on to other components of the device 1005. The input module 1010 may utilize a single antenna or a set of multiple antennas.

The output module 1015 may provide a means for transmitting signals generated by other components of the device 1005. For example, the output module 1015 may transmit information such as packets, user data, control information, or any combination thereof associated with various information channels (e.g., control channels, data channels, information channels related to illness detection techniques). In some examples, the output module 1015 may be co-located with the input module 1010 in a transceiver module. The output module 1015 may utilize a single antenna or a set of multiple antennas.

For example, the wearable application 1020 may include a physiological data component 1025, a condition quality component 1030, a PPG data component 1035, a heart rate component 1040, or any combination thereof. In some examples, the wearable application 1020, or various components thereof, may be configured to perform various operations (e.g., receiving, monitoring, transmitting) using or otherwise in cooperation with the input module 1010, the output module 1015, or both. For example, the wearable application 1020 may receive information from the input module 1010, send information to the output module 1015, or be integrated in combination with the input module 1010, the output module 1015, or both to receive information, transmit information, or perform various other operations as described herein.

The physiological data component 1025 may be configured as or otherwise support a means for receiving physiological data associated with the user, the physiological data comprising motion data and temperature data collected throughout a time interval via a wearable device associated with the user. The condition quality component 1030 may be configured as or otherwise support a means for determining a condition quality metric associated with the time interval based at least in part on the received motion data and temperature data, the condition quality metric indicating a relative quality of the physiological data collected throughout the time interval for determination of heart rate measurements. The PPG data component 1035 may be configured as or otherwise support a means for sampling PPG data for the user via the wearable device based at least in part on the condition quality metric satisfying a threshold metric value and a timer satisfying a first threshold time duration. The heart rate component 1040 may be configured as or otherwise support a means for determining a heart rate measurement for the user based at least in part on the sampled PPG data.

Figure 11:
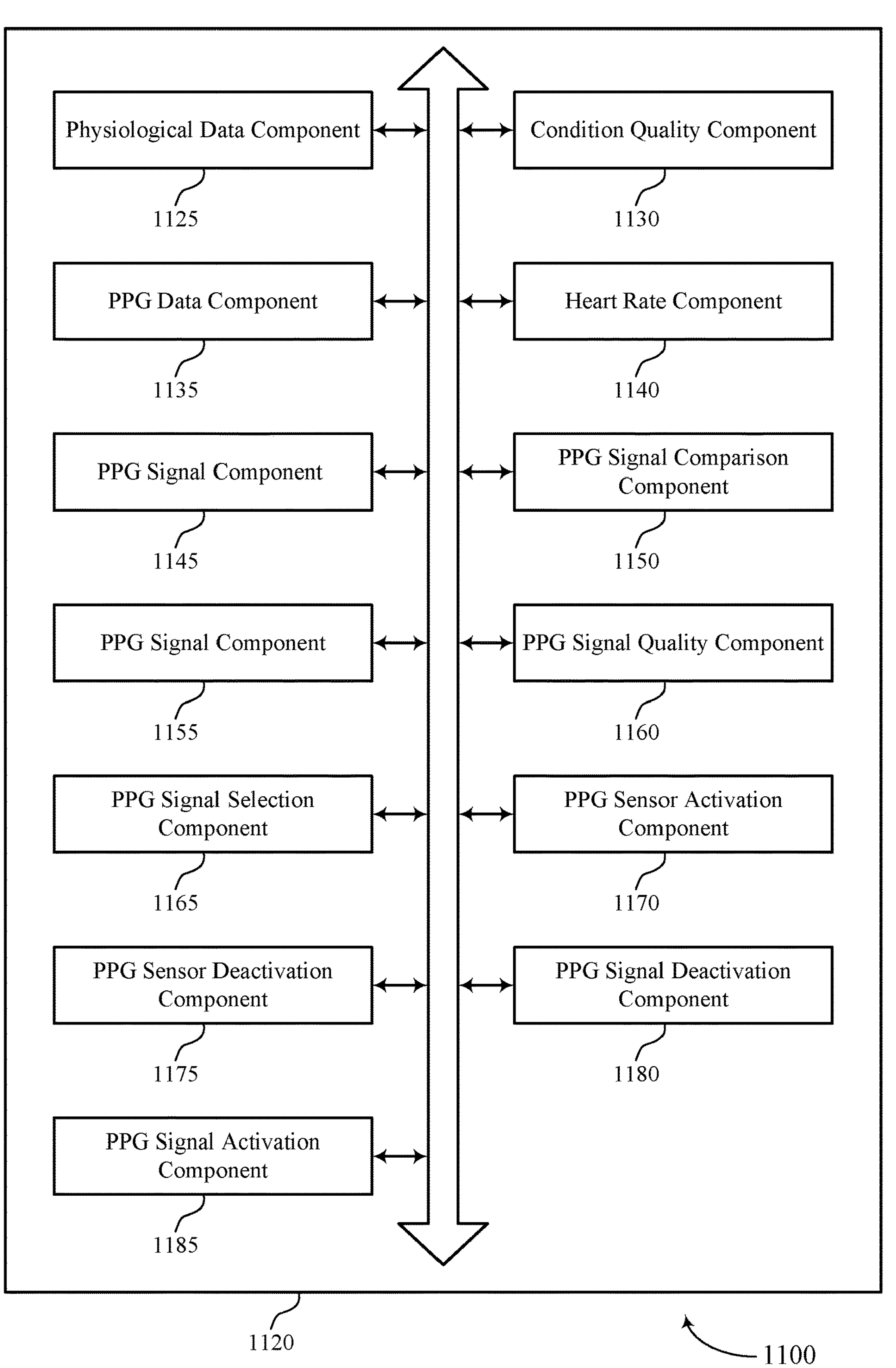
FIG. 11 shows a block diagram of a wearable application that supports techniques for heart rate detection in accordance with aspects of the present disclosure.

FIG. 11 shows a block diagram 1100 of a wearable application 1120 that supports techniques for heart rate detection in accordance with aspects of the present disclosure. The wearable application 1120 may be an example of aspects of a wearable application or a wearable application 1020, or both, as described herein. The wearable application 1120, or various components thereof, may be an example of means for performing various aspects of techniques for heart rate detection as described herein. For example, the wearable application 1120 may include a physiological data component 1125, a condition quality component 1130, a PPG data component 1135, a heart rate component 1140, a PPG signal component 1145, a PPG signal comparison component 1150, a PPG signal component 1155, a PPG signal quality component 1160, a PPG signal selection component 1165, a PPG sensor activation component 1170, a PPG sensor deactivation component 1175, a PPG signal deactivation component 1180, a PPG signal activation component 1185, or any combination thereof. Each of these components may communicate, directly or indirectly, with one another (e.g., via one or more buses).

The physiological data component 1125 may be configured as or otherwise support a means for receiving physiological data associated with the user, the physiological data comprising motion data and temperature data collected throughout a time interval via a wearable device associated with the user. The condition quality component 1130 may be configured as or otherwise support a means for determining a condition quality metric associated with the time interval based at least in part on the received motion data and temperature data, the condition quality metric indicating a relative quality of the physiological data collected throughout the time interval for determination of heart rate measurements. The PPG data component 1135 may be configured as or otherwise support a means for sampling PPG data for the user via the wearable device based at least in part on the condition quality metric satisfying a threshold metric value and a timer satisfying a first threshold time duration. The heart rate component 1140 may be configured as or otherwise support a means for determining a heart rate measurement for the user based at least in part on the sampled PPG data.

In some examples, to support sampling the PPG data, the PPG signal component 1145 may be configured as or otherwise support a means for acquiring a first PPG signal via a first pair of PPG sensors including at least a light-emitting diode configured to emit light within a visible spectrum. In some examples, to support sampling the PPG data, the PPG signal component 1145 may be configured as or otherwise support a means for acquiring a second PPG signal via a second pair of PPG sensors including at least an infrared diode. In some examples, to support sampling the PPG data, the PPG signal comparison component 1150 may be configured as or otherwise support a means for comparing a first PPG quality metric associated with the first PPG signal and a second PPG quality metric associated with the second PPG signal, the first and second PPG quality metrics indicating relative qualities of the first and second PPG signals, respectively, wherein determining the heart rate measurement is based at least in part on the comparison.

In some examples, the PPG signal selection component 1165 may be configured as or otherwise support a means for selecting one of the first or second PPG signal based at least in part on the comparison, wherein the heart rate measurement is determined based at least in part on the selected first or second PPG signal.

In some examples, the PPG signal deactivation component 1180 may be configured as or otherwise support a means for selectively deactivating the other of the first or second PPG signal that was not selected, wherein determining the heart rate measurement is based at least in part on selectively deactivating the other of the first or second PPG signal.

In some examples, the PPG signal component 1155 may be configured as or otherwise support a means for acquiring an additional PPG signal via one of the first or second pairs of PPG sensors associated with the selected one of the first or second PPG signals based at least in part on the selecting, wherein the heart rate measurement is based at least in part on the additional PPG signal.

In some examples, the PPG signal activation component 1185 may be configured as or otherwise support a means for selectively activating the other of the first or second PPG signal that was not selected based at least in part on the additional PPG signal failing to satisfy a threshold quality metric. In some examples, the PPG signal component 1155 may be configured as or otherwise support a means for acquiring a third PPG signal via the other of the first or second PPG signal that was not selected based at least in part on activating the other of the first or second PPG signal that was not selected, wherein the heart rate measurement is based at least in part on the third PPG signal.

In some examples, to support sampling the PPG data, the PPG signal component 1155 may be configured as or otherwise support a means for acquiring a first PPG signal via a first pair of PPG sensors including at least an infrared diode. In some examples, to support sampling the PPG data, the PPG signal comparison component 1150 may be configured as or otherwise support a means for comparing a first PPG quality metric associated with the first PPG signal to a threshold quality metric, the first PPG quality metric indicating a relative quality of the first PPG signal, respectively, wherein determining the heart rate measurement is based at least in part on the comparison.

In some examples, the PPG signal component 1155 may be configured as or otherwise support a means for acquiring an additional PPG signal via the first pair of PPG sensors based at least in part on the first PPG quality metric associated with the first PPG signal satisfying the threshold quality metric, wherein the heart rate measurement is determined based at least in part on the additional PPG signal.

In some examples, the PPG sensor activation component 1170 may be configured as or otherwise support a means for selectively activating a second pair of PPG sensors including at least a light-emitting diode configured to emit light within a visible spectrum based at least in part on the first PPG quality metric associated with the first PPG signal failing to satisfy the threshold quality metric. In some examples, the PPG signal component 1155 may be configured as or otherwise support a means for acquiring a second PPG signal via the second pair of PPG sensors based at least in part on selectively activating the second pair of PPG sensors, wherein the heart rate measurement is determined based at least in part on the second PPG signal.

In some examples, the PPG sensor deactivation component 1175 may be configured as or otherwise support a means for selectively deactivating the first pair of PPG sensors based at least in part on the first PPG quality metric associated with the first PPG signal failing to satisfy the threshold quality metric, wherein determining the heart rate measurement is based at least in part on selectively deactivating the first pair of PPG sensors.

In some examples, the condition quality component 1130 may be configured as or otherwise support a means for determining a quantity of heart beats within the PPG signal, wherein the PPG quality metric associated with the PPG signal is based at least in part on the quantity of heart beats.

In some examples, the PPG signal quality component 1160 may be configured as or otherwise support a means for determining a quantity of heart beats within the PPG signal, wherein the PPG quality metric associated with the PPG signal is based at least in part on the quantity of heart beats.

In some examples, to support sampling the PPG data, the PPG signal component 1155 may be configured as or otherwise support a means for acquiring a first PPG signal throughout the time interval. In some examples, to support sampling the PPG data, the PPG signal quality component 1160 may be configured as or otherwise support a means for determining that a first PPG quality metric associated with the first PPG signal satisfies a first threshold quality metric, wherein determining the heart rate measurement is based at least in part on the first PPG quality metric satisfying the threshold quality metric.

In some examples, the PPG signal component 1155 may be configured as or otherwise support a means for acquiring a second PPG signal throughout a second time interval subsequent to the first time interval. In some examples, the PPG signal quality component 1160 may be configured as or otherwise support a means for determining that a second PPG quality metric associated with the second PPG signal fails to satisfy the first threshold quality metric. In some examples, the heart rate component 1140 may be configured as or otherwise support a means for determining a second heart rate measurement for the user for the second time interval based at least in part on the second PPG quality metric satisfying a second threshold quality metric that is less than the first threshold quality metric.

In some examples, the wearable device comprises a wearable ring device. In some examples, the wearable device collects the physiological data from the user based on arterial blood flow.

Figure 12:
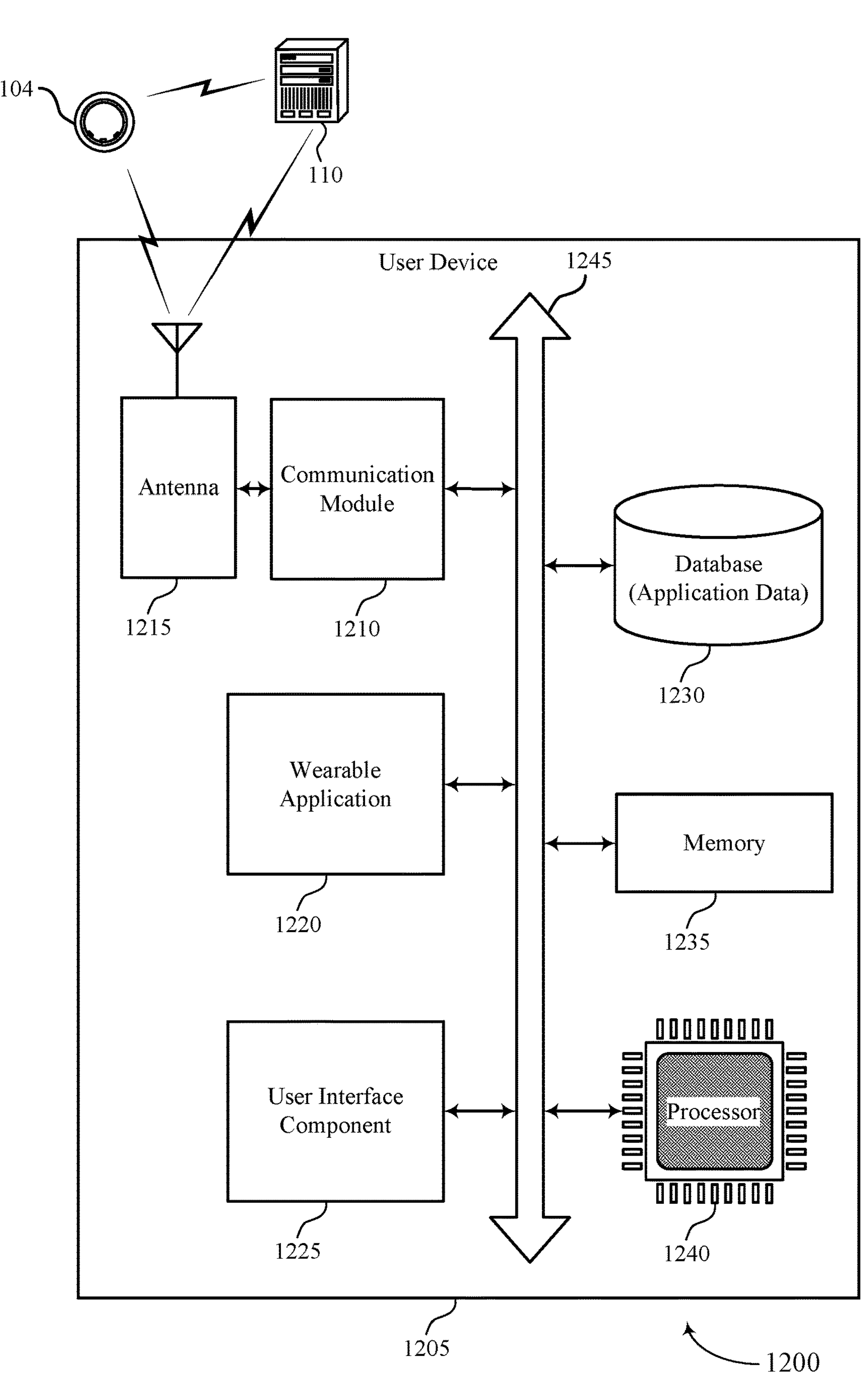
FIG. 12 shows a diagram of a system including a device that supports techniques for heart rate detection in accordance with aspects of the present disclosure.

FIG. 12 shows a diagram of a system 1200 including a device 1205 that supports techniques for heart rate detection in accordance with aspects of the present disclosure. The device 1205 may be an example of or include the components of a device 1005 as described herein. The device 1205 may include an example of a user device 106, as described previously herein. The device 1205 may include components for bi-directional communications including components for transmitting and receiving communications with a wearable device 104 and a server 110, such as a wearable application 1220, a communication module 1210, an antenna 1215, a user interface component 1225, a database (application data) 1230, a memory 1235, and a processor 1240. These components may be in electronic communication or otherwise coupled (e.g., operatively, communicatively, functionally, electronically, electrically) via one or more buses (e.g., a bus 1245).

The communication module 1210 may manage input and output signals for the device 1205 via the antenna 1215. The communication module 1210 may include an example of the communication module 220-*b* of the user device 106 shown and described in FIG. 2. In this regard, the communication module 1210 may manage communications with the ring 104 and the server 110, as illustrated in FIG. 2. The communication module 1210 may also manage peripherals not integrated into the device 1205. In some cases, the communication module 1210 may represent a physical connection or port to an external peripheral. In some cases, the communication module 1210 may utilize an operating system such as iOS®, ANDROID®, MS-DOS®, MS-WINDOWS®, OS/2®, UNIX®, LINUX®, or another known operating system. In other cases, the communication module 1210 may represent or interact with a wearable device (e.g., ring 104), modem, a keyboard, a mouse, a touchscreen, or a similar device. In some cases, the communication module 1210 may be implemented as part of the processor 1240. In some examples, a user may interact with the device 1205 via the communication module 1210, user interface component 1225, or via hardware components controlled by the communication module 1210.

In some cases, the device 1205 may include a single antenna 1215. However, in some other cases, the device 1205 may have more than one antenna 1215, which may be capable of concurrently transmitting or receiving multiple wireless transmissions. The communication module 1210 may communicate bi-directionally, via the one or more antennas 1215, wired, or wireless links as described herein. For example, the communication module 1210 may represent a wireless transceiver and may communicate bi-directionally with another wireless transceiver. The communication module 1210 may also include a modem to modulate the packets, to provide the modulated packets to one or more antennas 1215 for transmission, and to demodulate packets received from the one or more antennas 1215.

The user interface component 1225 may manage data storage and processing in a database 1230. In some cases, a user may interact with the user interface component 1225. In other cases, the user interface component 1225 may operate automatically without user interaction. The database 1230 may be an example of a single database, a distributed database, multiple distributed databases, a data store, a data lake, or an emergency backup database.

The memory 1235 may include RAM and ROM. The memory 1235 may store computer-readable, computer-executable software including instructions that, when executed, cause the processor 1240 to perform various functions described herein. In some cases, the memory 1235 may contain, among other things, a BIOS which may control basic hardware or software operation such as the interaction with peripheral components or devices.

The processor 1240 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1240 may be configured to operate a memory array using a memory controller. In other cases, a memory controller may be integrated into the processor 1240. The processor 1240 may be configured to execute computer-readable instructions stored in a memory 1235 to perform various functions (e.g., functions or tasks supporting a method and system for sleep staging algorithms).

For example, the wearable application 1220 may be configured as or otherwise support a means for receiving physiological data associated with the user, the physiological data comprising motion data and temperature data collected throughout a time interval via a wearable device associated with the user. The wearable application 1220 may be configured as or otherwise support a means for determining a condition quality metric associated with the time interval based at least in part on the received motion data and temperature data, the condition quality metric indicating a relative quality of the physiological data collected throughout the time interval for determination of heart rate measurements. The wearable application 1220 may be configured as or otherwise support a means for sampling PPG data for the user via the wearable device based at least in part on the condition quality metric satisfying a threshold metric value and a timer satisfying a first threshold time duration. The wearable application 1220 may be configured as or otherwise support a means for determining a heart rate measurement for the user based at least in part on the sampled PPG data.

By including or configuring the wearable application 1220 in accordance with examples as described herein, the device 1205 may support techniques for improved heart rate data determination and output procedures.

The wearable application 1220 may include an application (e.g., "app"), program, software, or other component which is configured to facilitate communications with a ring 104, server 110, other user devices 106, and the like. For example, the wearable application 1220 may include an application executable on a user device 106 which is configured to receive data (e.g., physiological data) from a ring 104, perform processing operations on the received data, transmit and receive data with the servers 110, and cause presentation of data to a user 102.

Figure 13:
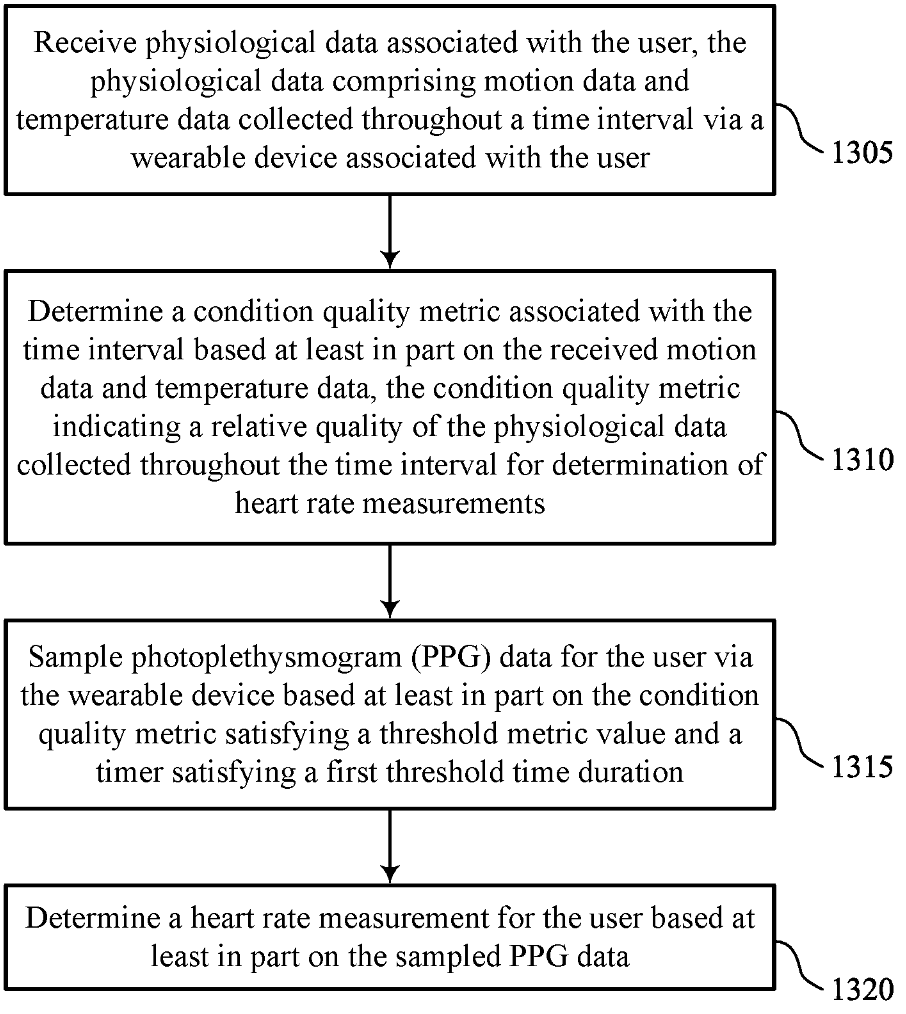
FIGS. 13 through 15 show flowcharts illustrating methods that support techniques for heart rate detection in accordance with aspects of the present disclosure.

FIG. 13 shows a flowchart illustrating a method 1300 that supports techniques for heart rate detection in accordance with aspects of the present disclosure. The operations of the method 1300 may be implemented by a user device or its components as described herein. For example, the operations of the method 1300 may be performed by a user device as described with reference to FIGS. 1 through 12. In some examples, a user device may execute a set of instructions to control the functional elements of the user device to perform the described functions. Additionally or alternatively, the user device may perform aspects of the described functions using special-purpose hardware.

At 1305, the method may include receiving physiological data associated with the user, the physiological data comprising motion data and temperature data collected throughout a time interval via a wearable device associated with the user. The operations of 1305 may be performed in accordance with examples as disclosed herein. In some examples, aspects of the operations of 1305 may be performed by a physiological data component 1125 as described with reference to FIG. 11.

At 1310, the method may include determining a condition quality metric associated with the time interval based at least in part on the received motion data and temperature data, the condition quality metric indicating a relative quality of the physiological data collected throughout the time interval for determination of heart rate measurements. The operations of 1310 may be performed in accordance with examples as disclosed herein. In some examples, aspects of the operations of 1310 may be performed by a condition quality component 1130 as described with reference to FIG. 11.

At 1315, the method may include sampling PPG data for the user via the wearable device based at least in part on the condition quality metric satisfying a threshold metric value and a timer satisfying a first threshold time duration. The operations of 1315 may be performed in accordance with examples as disclosed herein. In some examples, aspects of the operations of 1315 may be performed by a PPG data component 1135 as described with reference to FIG. 11.

At 1320, the method may include determining a heart rate measurement for the user based at least in part on the sampled PPG data. The operations of 1320 may be performed in accordance with examples as disclosed herein. In some examples, aspects of the operations of 1320 may be performed by a heart rate component 1140 as described with reference to FIG. 11.

Figure 14:
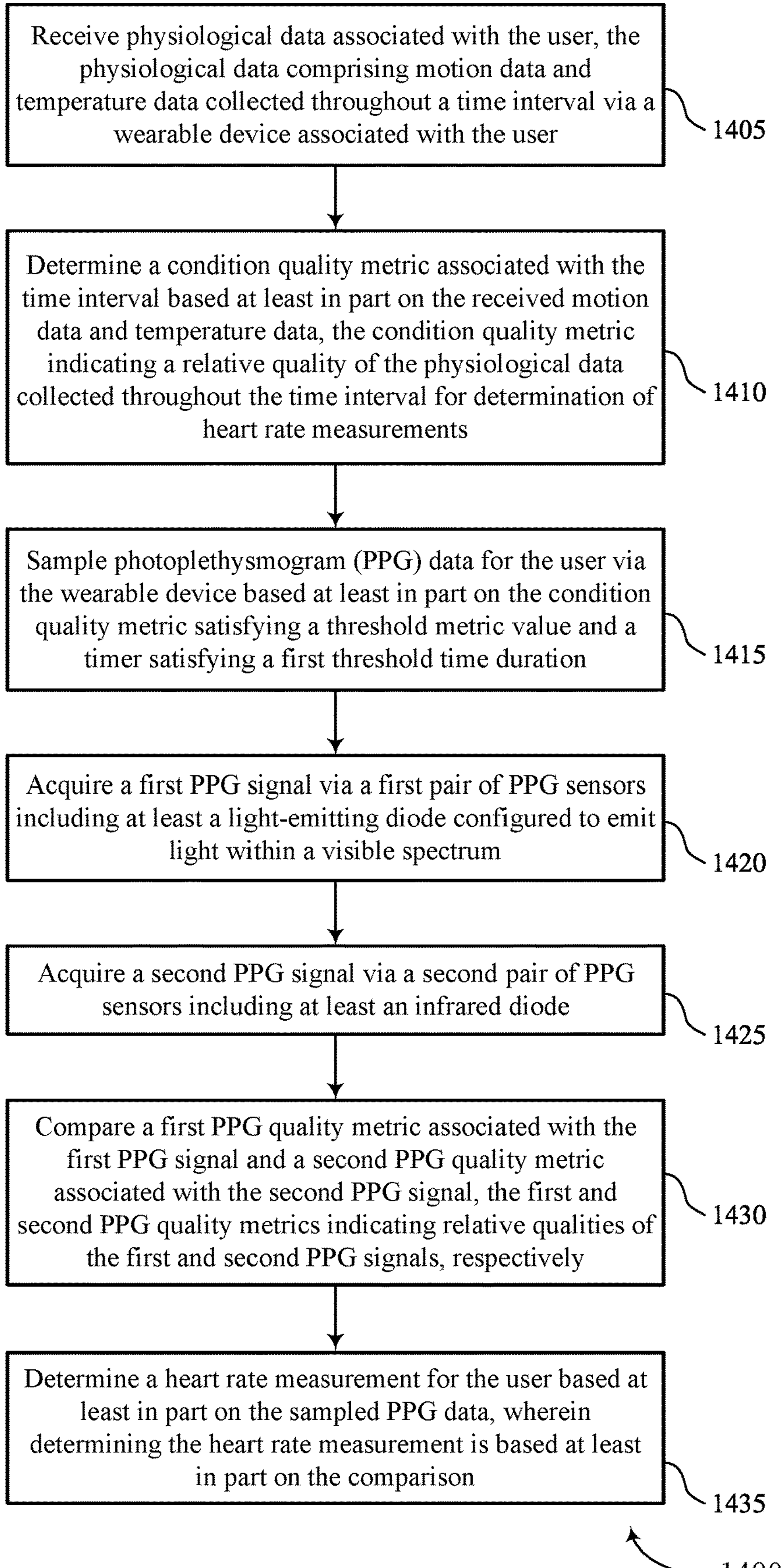

FIG. 14 shows a flowchart illustrating a method 1400 that supports techniques for heart rate detection in accordance with aspects of the present disclosure. The operations of the method 1400 may be implemented by a user device or its components as described herein. For example, the operations of the method 1400 may be performed by a user device as described with reference to FIGS. 1 through 12. In some examples, a user device may execute a set of instructions to control the functional elements of the user device to perform the described functions. Additionally or alternatively, the user device may perform aspects of the described functions using special-purpose hardware.

At 1405, the method may include receiving physiological data associated with the user, the physiological data comprising motion data and temperature data collected throughout a time interval via a wearable device associated with the user. The operations of 1405 may be performed in accordance with examples as disclosed herein. In some examples, aspects of the operations of 1405 may be performed by a physiological data component 1125 as described with reference to FIG. 11.

At 1410, the method may include determining a condition quality metric associated with the time interval based at least in part on the received motion data and temperature data, the condition quality metric indicating a relative quality of the physiological data collected throughout the time interval for determination of heart rate measurements. The operations of 1410 may be performed in accordance with examples as disclosed herein. In some examples, aspects of the operations of 1410 may be performed by a condition quality component 1130 as described with reference to FIG. 11.

At 1415, the method may include sampling PPG data for the user via the wearable device based at least in part on the condition quality metric satisfying a threshold metric value and a timer satisfying a first threshold time duration. The operations of 1415 may be performed in accordance with examples as disclosed herein. In some examples, aspects of the operations of 1415 may be performed by a PPG data component 1135 as described with reference to FIG. 11.

At 1420, the method may include acquiring a first PPG signal via a first pair of PPG sensors including at least a light-emitting diode configured to emit light within a visible spectrum. The operations of 1420 may be performed in accordance with examples as disclosed herein. In some examples, aspects of the operations of 1420 may be performed by a PPG signal component 1145 as described with reference to FIG. 11.

At 1425, the method may include acquiring a second PPG signal via a second pair of PPG sensors including at least an infrared diode. The operations of 1425 may be performed in accordance with examples as disclosed herein. In some examples, aspects of the operations of 1425 may be performed by a PPG signal component 1145 as described with reference to FIG. 11.

At 1430, the method may include comparing a first PPG quality metric associated with the first PPG signal and a second PPG quality metric associated with the second PPG signal, the first and second PPG quality metrics indicating relative qualities of the first and second PPG signals, respectively. The operations of 1430 may be performed in accordance with examples as disclosed herein. In some examples, aspects of the operations of 1430 may be performed by a PPG signal comparison component 1150 as described with reference to FIG. 11.

At 1435, the method may include determining a heart rate measurement for the user based at least in part on the sampled PPG data, wherein determining the heart rate measurement is based at least in part on the comparison. The operations of 1435 may be performed in accordance with examples as disclosed herein. In some examples, aspects of the operations of 1435 may be performed by a heart rate component 1140 as described with reference to FIG. 11.

Figure 15:
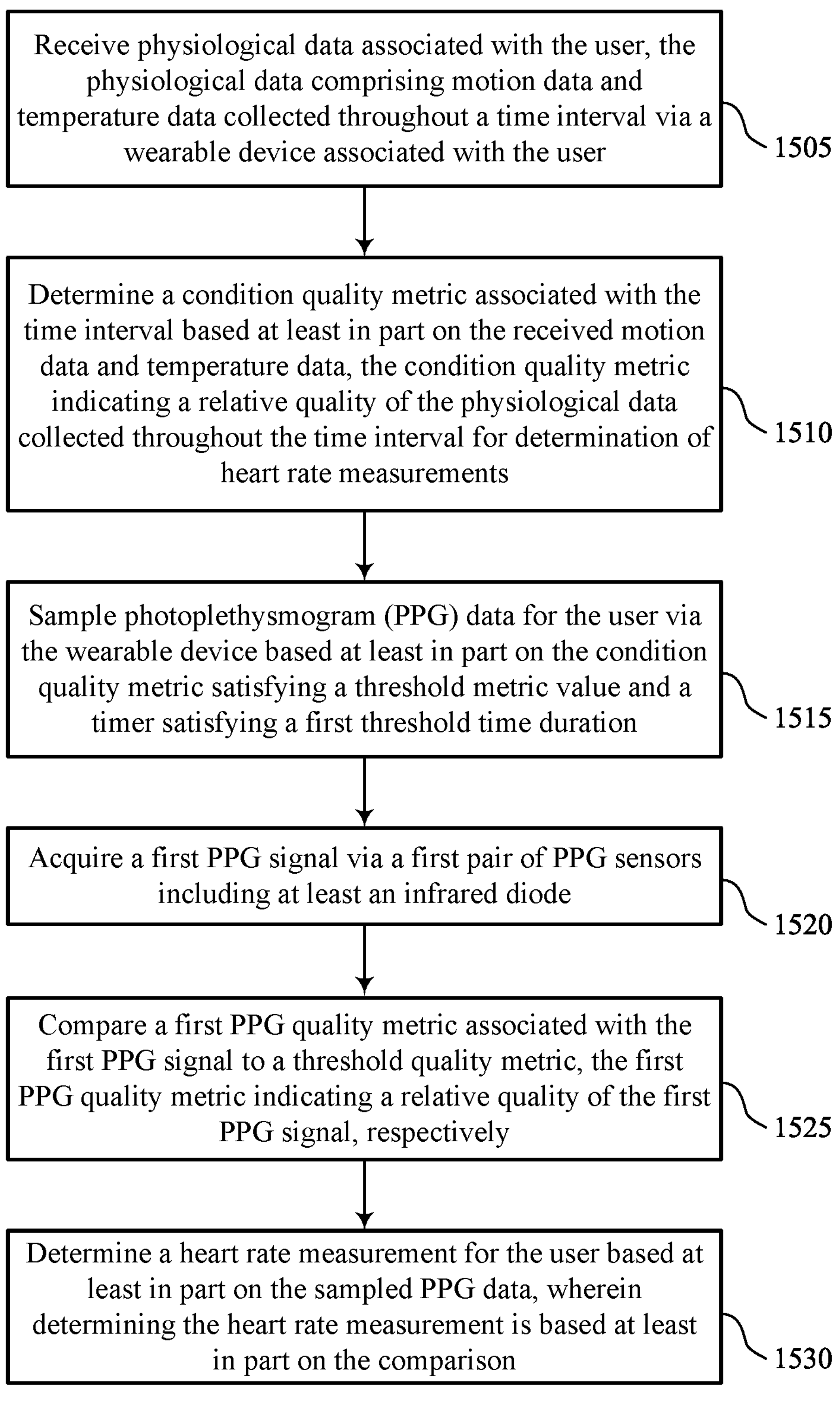

FIG. 15 shows a flowchart illustrating a method 1500 that supports techniques for heart rate detection in accordance with aspects of the present disclosure. The operations of the method 1500 may be implemented by a user device or its components as described herein. For example, the operations of the method 1500 may be performed by a user device as described with reference to FIGS. 1 through 12. In some examples, a user device may execute a set of instructions to control the functional elements of the user device to perform the described functions. Additionally or alternatively, the user device may perform aspects of the described functions using special-purpose hardware.

At 1505, the method may include receiving physiological data associated with the user, the physiological data comprising motion data and temperature data collected throughout a time interval via a wearable device associated with the user. The operations of 1505 may be performed in accordance with examples as disclosed herein. In some examples, aspects of the operations of 1505 may be performed by a physiological data component 1125 as described with reference to FIG. 11.

At 1510, the method may include determining a condition quality metric associated with the time interval based at least in part on the received motion data and temperature data, the condition quality metric indicating a relative quality of the physiological data collected throughout the time interval for determination of heart rate measurements. The operations of 1510 may be performed in accordance with examples as disclosed herein. In some examples, aspects of the operations of 1510 may be performed by a condition quality component 1130 as described with reference to FIG. 11.

At 1515, the method may include sampling PPG data for the user via the wearable device based at least in part on the condition quality metric satisfying a threshold metric value and a timer satisfying a first threshold time duration. The operations of 1515 may be performed in accordance with examples as disclosed herein. In some examples, aspects of the operations of 1515 may be performed by a PPG data component 1135 as described with reference to FIG. 11.

At 1520, the method may include acquiring a first PPG signal via a first pair of PPG sensors including at least an infrared diode. The operations of 1520 may be performed in accordance with examples as disclosed herein. In some examples, aspects of the operations of 1520 may be performed by a PPG signal component 1155 as described with reference to FIG. 11.

At 1525, the method may include comparing a first PPG quality metric associated with the first PPG signal to a threshold quality metric, the first PPG quality metric indicating a relative quality of the first PPG signal, respectively. The operations of 1525 may be performed in accordance with examples as disclosed herein. In some examples, aspects of the operations of 1525 may be performed by a PPG signal comparison component 1150 as described with reference to FIG. 11.

At 1530, the method may include determining a heart rate measurement for the user based at least in part on the sampled PPG data, wherein determining the heart rate measurement is based at least in part on the comparison. The operations of 1530 may be performed in accordance with examples as disclosed herein. In some examples, aspects of the operations of 1530 may be performed by a heart rate component 1140 as described with reference to FIG. 11.

It should be noted that the methods described above describe possible implementations, and that the operations and the steps may be rearranged or otherwise modified and that other implementations are possible. Furthermore, aspects from two or more of the methods may be combined.

A method is described. The method may include receiving physiological data associated with the user, the physiological data comprising motion data and temperature data collected throughout a time interval via a wearable device associated with the user, determining a condition quality metric associated with the time interval based at least in part on the received motion data and temperature data, the condition quality metric indicating a relative quality of the physiological data collected throughout the time interval for determination of heart rate measurements, sampling PPG data for the user via the wearable device based at least in part on the condition quality metric satisfying a threshold metric value and a timer satisfying a first threshold time duration, and determining a heart rate measurement for the user based at least in part on the sampled PPG data.

An apparatus is described. The apparatus may include a processor, memory coupled with the processor, and instructions stored in the memory. The instructions may be executable by the processor to cause the apparatus to receive physiological data associated with the user, the physiological data comprising motion data and temperature data collected throughout a time interval via a wearable device associated with the user, determine a condition quality metric associated with the time interval based at least in part on the received motion data and temperature data, the condition quality metric indicating a relative quality of the physiological data collected throughout the time interval for determination of heart rate measurements, sample photoplethysmogram (PPG) data for the user via the wearable device based at least in part on the condition quality metric satisfying a threshold metric value and a timer satisfying a first threshold time duration, and determine a heart rate measurement for the user based at least in part on the sampled PPG data.

Another apparatus is described. The apparatus may include means for receiving physiological data associated with the user, the physiological data comprising motion data and temperature data collected throughout a time interval via a wearable device associated with the user, means for determining a condition quality metric associated with the time interval based at least in part on the received motion data and temperature data, the condition quality metric indicating a relative quality of the physiological data collected throughout the time interval for determination of heart rate measurements, means for sampling PPG data for the user via the wearable device based at least in part on the condition quality metric satisfying a threshold metric value and a timer satisfying a first threshold time duration, and means for determining a heart rate measurement for the user based at least in part on the sampled PPG data.

A non-transitory computer-readable medium storing code is described. The code may include instructions executable by a processor to receive physiological data associated with the user, the physiological data comprising motion data and temperature data collected throughout a time interval via a wearable device associated with the user, determine a condition quality metric associated with the time interval based at least in part on the received motion data and temperature data, the condition quality metric indicating a relative quality of the physiological data collected throughout the time interval for determination of heart rate measurements, sample PPG data for the user via the wearable device based at least in part on the condition quality metric satisfying a threshold metric value and a timer satisfying a first threshold time duration, and determine a heart rate measurement for the user based at least in part on the sampled PPG data.

In some examples of the method, apparatuses, and non-transitory computer-readable medium described herein, sampling the PPG data may include operations, features, means, or instructions for acquiring a first PPG signal via a first pair of PPG sensors including at least a light-emitting diode configured to emit light within a visible spectrum, acquiring a second PPG signal via a second pair of PPG sensors including at least an infrared diode, and comparing a first PPG quality metric associated with the first PPG signal and a second PPG quality metric associated with the second PPG signal, the first and second PPG quality metrics indicating relative qualities of the first and second PPG signals, respectively, wherein determining the heart rate measurement may be based at least in part on the comparison.

Some examples of the method, apparatuses, and non-transitory computer-readable medium described herein may further include operations, features, means, or instructions for selecting one of the first or second PPG signal based at least in part on the comparison, wherein the heart rate measurement may be determined based at least in part on the selected first or second PPG signal.

In some examples of the method, apparatuses, and non-transitory computer-readable medium described herein, selectively deactivating the other of the first or second PPG signal that was not selected, wherein determining the heart rate measurement may be based at least in part on selectively deactivating the other of the first or second PPG signal.

Some examples of the method, apparatuses, and non-transitory computer-readable medium described herein may further include operations, features, means, or instructions for acquiring an additional PPG signal via one of the first or second pairs of PPG sensors associated with the selected one of the first or second PPG signals based at least in part on the selecting, wherein the heart rate measurement may be based at least in part on the additional PPG signal.

In some examples of the method, apparatuses, and non-transitory computer-readable medium described herein, selectively activating the other of the first or second PPG signal that was not selected based at least in part on the additional PPG signal failing to satisfy a threshold quality metric and acquiring a third PPG signal via the other of the first or second PPG signal that was not selected based at least in part on activating the other of the first or second PPG signal that was not selected, wherein the heart rate measurement may be based at least in part on the third PPG signal.

In some examples of the method, apparatuses, and non-transitory computer-readable medium described herein, sampling the PPG data may include operations, features, means, or instructions for acquiring a first PPG signal via a first pair of PPG sensors including at least an infrared diode and comparing a first PPG quality metric associated with the first PPG signal to a threshold quality metric, the first PPG quality metric indicating a relative quality of the first PPG signal, respectively, wherein determining the heart rate measurement may be based at least in part on the comparison.

Some examples of the method, apparatuses, and non-transitory computer-readable medium described herein may further include operations, features, means, or instructions for acquiring an additional PPG signal via the first pair of PPG sensors based at least in part on the first PPG quality metric associated with the first PPG signal satisfying the threshold quality metric, wherein the heart rate measurement may be determined based at least in part on the additional PPG signal.

In some examples of the method, apparatuses, and non-transitory computer-readable medium described herein, selectively activating a second pair of PPG sensors including at least a light-emitting diode configured to emit light within a visible spectrum based at least in part on the first PPG quality metric associated with the first PPG signal failing to satisfy the threshold quality metric and acquiring a second PPG signal via the second pair of PPG sensors based at least in part on selectively activating the second pair of PPG sensors, wherein the heart rate measurement may be determined based at least in part on the second PPG signal.

In some examples of the method, apparatuses, and non-transitory computer-readable medium described herein, selectively deactivating the first pair of PPG sensors based at least in part on the first PPG quality metric associated with the first PPG signal failing to satisfy the threshold quality metric, wherein determining the heart rate measurement may be based at least in part on selectively deactivating the first pair of PPG sensors.

Some examples of the method, apparatuses, and non-transitory computer-readable medium described herein may further include operations, features, means, or instructions for determining a quantity of heart beats within the PPG signal, wherein the PPG quality metric associated with the PPG signal may be based at least in part on the quantity of heart beats.

Some examples of the method, apparatuses, and non-transitory computer-readable medium described herein may further include operations, features, means, or instructions for determining a quantity of heart beats within the PPG signal, wherein the PPG quality metric associated with the PPG signal may be based at least in part on the quantity of heart beats.

In some examples of the method, apparatuses, and non-transitory computer-readable medium described herein, sampling the PPG data may include operations, features, means, or instructions for acquiring a first PPG signal throughout the time interval and determining that a first PPG quality metric associated with the first PPG signal satisfies a first threshold quality metric, wherein determining the heart rate measurement may be based at least in part on the first PPG quality metric satisfying the threshold quality metric.

Some examples of the method, apparatuses, and non-transitory computer-readable medium described herein may further include operations, features, means, or instructions for acquiring a second PPG signal throughout a second time interval subsequent to the first time interval, determining that a second PPG quality metric associated with the second PPG signal fails to satisfy the first threshold quality metric, and determining a second heart rate measurement for the user for the second time interval based at least in part on the second PPG quality metric satisfying a second threshold quality metric that may be less than the first threshold quality metric.

In some examples of the method, apparatuses, and non-transitory computer-readable medium described herein, the wearable device comprises a wearable ring device.

In some examples of the method, apparatuses, and non-transitory computer-readable medium described herein, the wearable device collects the physiological data from the user based on arterial blood flow.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for measuring heart rate for a user comprising:

receiving physiological data associated with the user, the physiological data comprising motion data and temperature data collected throughout a time interval via a wearable device associated with the user;

determining a condition quality metric associated with the time interval based at least in part on the received motion data and temperature data, the condition quality metric indicating a relative quality of the physiological data collected throughout the time interval for determination of heart rate measurements;

initiating sampling of photoplethysmogram (PPG) data for the user via the wearable device based at least in part on the condition quality metric satisfying a threshold metric value and an elapsed time since a previous sampling of PPG data satisfying a first threshold time duration; and determining a heart rate measurement for the user based at least in part on the sampled PPG data.

2. The method of claim 1, wherein initiating sampling of the PPG data comprises:

acquiring a first PPG signal via a first pair of PPG sensors including at least a light-emitting diode configured to emit light within a visible spectrum;

acquiring a second PPG signal via a second pair of PPG sensors including at least an infrared diode; and comparing a first PPG quality metric associated with the first PPG signal and a second PPG quality metric associated with the second PPG signal, the first and second PPG quality metrics indicating relative qualities of the first and second PPG signals, respectively, wherein determining the heart rate measurement is based at least in part on the comparison.

3. The method of claim 2, further comprising:

selecting one of the first or second PPG signal based at least in part on the comparison, wherein the heart rate measurement is determined based at least in part on the selected first or second PPG signal.

4. The method of claim 3, further comprising:

selectively deactivating the other of the first or second PPG signal that was not selected, wherein determining the heart rate measurement is based at least in part on selectively deactivating the other of the first or second PPG signal.

5. The method of claim 3, further comprising:

acquiring an additional PPG signal via one of the first or second pairs of PPG sensors associated with the selected one of the first or second PPG signals based at least in part on the selecting, wherein the heart rate measurement is based at least in part on the additional PPG signal.

6. The method of claim 5, further comprising:

selectively activating the other of the first or second PPG signal that was not selected based at least in part on the additional PPG signal failing to satisfy a threshold quality metric; and acquiring a third PPG signal via the other of the first or second PPG signal that was not selected based at least in part on activating the other of the first or second PPG signal that was not selected, wherein the heart rate measurement is based at least in part on the third PPG signal.

7. The method of claim 1, wherein initiating sampling of the PPG data comprises:

acquiring a first PPG signal via a first pair of PPG sensors including at least an infrared diode; and comparing a first PPG quality metric associated with the first PPG signal to a threshold quality metric, the first PPG quality metric indicating a relative quality of the first PPG signal, respectively, wherein determining the heart rate measurement is based at least in part on the comparison.

8. The method of claim 7, further comprising:

acquiring an additional PPG signal via the first pair of PPG sensors based at least in part on the first PPG quality metric associated with the first PPG signal satisfying the threshold quality metric, wherein the heart rate measurement is determined based at least in part on the additional PPG signal.

9. The method of claim 7, further comprising:

selectively activating a second pair of PPG sensors including at least a light-emitting diode configured to emit light within a visible spectrum based at least in part on the first PPG quality metric associated with the first PPG signal failing to satisfy the threshold quality metric; and acquiring a second PPG signal via the second pair of PPG sensors based at least in part on selectively activating the second pair of PPG sensors, wherein the heart rate measurement is determined based at least in part on the second PPG signal.

10. The method of claim 7, further comprising:

selectively deactivating the first pair of PPG sensors based at least in part on the first PPG quality metric associated with the first PPG signal failing to satisfy the threshold quality metric, wherein determining the heart rate measurement is based at least in part on selectively deactivating the first pair of PPG sensors.

11. The method of claim 7, further comprising:

determining a quantity of heart beats within the first PPG signal, wherein the first PPG quality metric associated with the first PPG signal is based at least in part on the quantity of heart beats.

12. The method of claim 1, wherein the condition quality metric satisfies the threshold metric value based at least in part on the motion data being less than or equal to a motion threshold, and the temperature data being greater than or equal to a temperature threshold.

13. The method of claim 1, wherein initiating sampling of the PPG data comprises:

acquiring a first PPG signal throughout a first time interval; and determining that a first PPG quality metric associated with the first PPG signal satisfies a first threshold quality metric, wherein determining the heart rate measurement is based at least in part on the first PPG quality metric satisfying the first threshold quality metric.

14. The method of claim 13, further comprising:

acquiring a second PPG signal throughout a second time interval subsequent to the first time interval;

determining that a second PPG quality metric associated with the second PPG signal fails to satisfy the first threshold quality metric; and determining a second heart rate measurement for the user for the second time interval based at least in part on the second PPG quality metric satisfying a second threshold quality metric that is less than the first threshold quality metric.

15. The method of claim 1, wherein the wearable device comprises a wearable ring device.

16. The method of claim 1, wherein the wearable device collects the physiological data from the user based on arterial blood flow.

17. An apparatus for measuring heart rate for a user, comprising:

one or more processors;

one or more memories coupled with the one or more processors; and instructions stored in the one or more memories and executable by the one or more processors to cause the apparatus to:

receive physiological data associated with the user, the physiological data comprising motion data and temperature data collected throughout a time interval via a wearable device associated with the user;

determine a condition quality metric associated with the time interval based at least in part on the received motion data and temperature data, the condition quality metric indicating a relative quality of the physiological data collected throughout the time interval for determination of heart rate measurements;

initiate sampling of photoplethysmogram (PPG) data for the user via the wearable device based at least in part on the condition quality metric satisfying a threshold metric value and an elapsed time since a previous sampling of PPG data satisfying a first threshold time duration; and determine a heart rate measurement for the user based at least in part on the sampled PPG data.

18. The apparatus of claim 17, wherein the instructions to initiate sampling of the PPG data are executable by the one or more processors to cause the apparatus to:

acquire a first PPG signal via a first pair of PPG sensors including at least a light-emitting diode configured to emit light within a visible spectrum;

acquire a second PPG signal via a second pair of PPG sensors including at least an infrared diode; and compare a first PPG quality metric associated with the first PPG signal and a second PPG quality metric associated with the second PPG signal, the first and second PPG quality metrics indicating relative qualities of the first and second PPG signals, respectively, wherein determining the heart rate measurement is based at least in part on the comparison.

19. The apparatus of claim 18, wherein the instructions are further executable by the one or more processors to cause the apparatus to:

select one of the first or second PPG signal based at least in part on the comparison, wherein the heart rate measurement is determined based at least in part on the selected first or second PPG signal.

20. The apparatus of claim 19, wherein the instructions are further executable by the one or more processors to cause the apparatus to:

selectively deactivate the other of the first or second PPG signal that was not selected, wherein determining the heart rate measurement is based at least in part on selectively deactivating the other of the first or second PPG signal.

* * * * *